(12) United States Patent
Furuya et al.

(10) Patent No.: US 12,252,586 B2
(45) Date of Patent: Mar. 18, 2025

(54) METHOD FOR SETTING CONDITIONS FOR USE OF POLYMERIZATION CATALYST, POLYMERIZATION CONDITION SETTING METHOD, AND METHOD FOR MANUFACTURING OPTICAL MATERIAL

(71) Applicant: MITSUI CHEMICALS, INC., Tokyo (JP)

(72) Inventors: Masayuki Furuya, Arao (JP); Takeshi Nishimura, Yanagawa (JP)

(73) Assignee: MITSUI CHEMICALS, INC., Tokyo (JP)

( * ) Notice: Subject to any disclaimer, the term of this patent is extended or adjusted under 35 U.S.C. 154(b) by 644 days.

(21) Appl. No.: 17/619,978

(22) PCT Filed: Jun. 18, 2020

(86) PCT No.: PCT/JP2020/023927
§ 371 (c)(1),
(2) Date: Dec. 16, 2021

(87) PCT Pub. No.: WO2020/256057
PCT Pub. Date: Dec. 24, 2020

(65) Prior Publication Data
US 2022/0372229 A1    Nov. 24, 2022

(30) Foreign Application Priority Data
Jun. 19, 2019    (JP) .................................. 2019-113432

(51) Int. Cl.
C08G 75/04    (2016.01)

(52) U.S. Cl.
CPC .......... *C08G 75/04* (2013.01); *C08G 2125/00* (2013.01)

(58) Field of Classification Search
CPC ..... C08G 75/04; C08G 18/7642; C08G 18/08
See application file for complete search history.

(56) References Cited

U.S. PATENT DOCUMENTS

| | | |
|---|---|---|
| 2010/0029890 A1 | 2/2010 | Kawato et al. |
| 2011/0112269 A1 | 5/2011 | Iwazumi et al. |
| 2011/0190466 A1 | 8/2011 | Hayashi et al. |
| 2017/0009002 A1 | 1/2017 | Tsukada et al. |
| 2017/0212054 A1* | 7/2017 | Reed ...................... B01J 8/1809 |
| 2019/0248949 A1 | 8/2019 | Ito et al. |

FOREIGN PATENT DOCUMENTS

| | | |
|---|---|---|
| JP | 2003252910 A | 9/2003 |
| JP | 5859556 B2 | 2/2016 |
| WO | 2007097116 A1 | 8/2007 |
| WO | 2008035457 A1 | 3/2008 |
| WO | 2010001550 A1 | 1/2010 |
| WO | 2013051292 A1 | 4/2013 |
| WO | 2015119220 A1 | 8/2015 |
| WO | 2018079829 A1 | 5/2018 |

OTHER PUBLICATIONS

Heidarian et al.-Study on kinetics of polymerization of dimer fatty acids with ethylenediamine in the presence of catalyst, Chemical Engineering Journal 100 (2004) 85-93, published on Feb. 2004.*

* cited by examiner

*Primary Examiner* — Gregory Listvoyb
(74) *Attorney, Agent, or Firm* — BUCHANAN INGERSOLL & ROONEY PC

(57) ABSTRACT

A method for setting conditions for use of a polymerization catalyst includes a step of acquiring a physical property value derived from remaining functional groups after maintaining a temperature of a composition including a polymerization-reactive compound and a predetermined amount of a polymerization catalyst, a step of calculating a remaining functional group ratio from the physical property value, a step of calculating a reaction rate constant based on a reaction rate equation from the remaining functional group ratio, a step of calculating an activation energy and a frequency factor from the reaction rate constant using an Arrhenius plot, a step of determining whether or not the activation energy satisfies a predetermined condition for the polymerization catalyst, a step of setting an approximation equation from the frequency factor, and a step of setting an addition range with respect to the polymerization-reactive compound.

13 Claims, 15 Drawing Sheets

METHOD FOR SETTING CONDITIONS FOR USE OF POLYMERIZATION CATALYST, POLYMERIZATION CONDITION SETTING METHOD, AND METHOD FOR MANUFACTURING OPTICAL MATERIAL

TECHNICAL FIELD

The present invention relates to a method for setting conditions for use of a polymerization catalyst, a polymerization condition setting method, and a method for manufacturing an optical material.

BACKGROUND ART

Plastic lenses are lighter and harder to break than inorganic lenses and are able to be dyed and have thus rapidly become widespread as optical materials for spectacle lenses and camera lenses and the like. So far, various molded articles for lenses have been developed and used.

Among these, typical examples include an allyl resin obtained from diethylene glycol bisallyl carbonate and diallyl isophthalate, a (meth)acrylic resin obtained from (meth)acrylate, a polythiourethane resin obtained from isocyanate and thiol, and the like.

Patent Documents 1 to 6 disclose polythiourethane resins obtained from a polymerizable composition including an isocyanate compound, a thiol compound, and a predetermined polymerization catalyst.

Patent Document 7 describes a method for determining the conditions for manufacturing a polymer by radical polymerization using a frequency factor and activation energy of an elementary reaction process of a polymerization reaction obtained by a reaction rate equation using catalyst concentration or the like, as well as the polymerization initial conditions or polymerization reaction control factors (temperature and the like) able to be changed during the reaction.

RELATED DOCUMENT

Patent Document

[Patent Document 1] International Publication No. 2007/097116
[Patent Document 2] International Publication No. 2008/035457
[Patent Document 3] International Publication No. 2010/001550
[Patent Document 4] International Publication No. 2013/051292
[Patent Document 5] International Publication No. 2015/119220
[Patent Document 6] International Publication No. 2018/079829
[Patent Document 7] Japanese Unexamined Patent Publication No. 2003-252910

SUMMARY OF THE INVENTION

Technical Problem

As disclosed in Patent Documents 1 to 6, plastic lenses are usually formed by polymerizing and curing a polymerizable composition including a polymerizable compound and a thermal polymerization catalyst or polymerization initiator (abbreviated below as "polymerization catalyst"), which are filled in a mold formed of a pair of glasses and a gasket or tape. Since the polymerization rate of the polymerizable composition varies depending on the kind and added amount of the polymerization catalyst, when the above are not optimized, partial variations in the polymerization rate may occur and optical distortion or striae may be generated in the plastic lens. Patent Document 7 does not describe a method for setting the kind and use amount of a polymerization catalyst.

The selection of the kind and added amount of the polymerization catalyst is an extremely important condition for suppressing optical distortion and striae. However, setting of the kind and added amount of the polymerization catalyst with respect to the polymerizable compounds has not yet been performed by reaction kinetic analysis.

An object of the present invention is to suppress optical distortion or striae accompanying the curing of a polymerizable composition, to determine the kind and addition range of a polymerization catalyst, with which an optical material having an excellent appearance is obtained, and to set conditions such as a polymerization program.

Solution to Problem

As a result of intensive studies performed by the present inventors, it was found that setting the kind and addition range of a polymerization catalyst with respect to a polymerizable compound according to a predetermined analysis makes it possible to suppress variation in the polymerization rate in a process of polymerizing and curing a polymerizable composition, and, as a result, it is possible to obtain an optical material having an excellent appearance in which the generation of optical distortion and striae is suppressed, thereby completing the present invention.

That is, it is possible to illustrate the present invention as follows.

[1] A method for setting conditions for use of a polymerization catalyst, the method including a physical property acquiring step of, when a composition 1 including a polymerization-reactive compound and a predetermined amount of a polymerization catalyst is heated and maintained at a plurality of temperatures, acquiring a physical property value 1a derived from functional groups of the polymerization-reactive compound before heating and a physical property value 1b derived from remaining functional groups after maintaining a temperature for a predetermined time, and, when a composition 2, which is different from the composition 1 only in an amount of the polymerization catalyst, is heated and maintained at the plurality of temperatures, acquiring a physical property value 2a derived from functional groups of the polymerization-reactive compound before heating and a physical property value 2b derived from remaining functional groups after maintaining a temperature for a predetermined time, a remaining functional group ratio calculating step of calculating a remaining functional group ratio 1 at the plurality of temperatures from the physical property value 1a and physical property value 1b, and calculating a remaining functional group ratio 2 at the plurality of temperatures from the physical property value 2a and physical property value 2b, a reaction rate constant calculating step of calculating a reaction rate constant 1 at the plurality of temperatures based on a reaction rate equation from the remaining functional group ratio 1, and calculating a reaction rate constant 2 at the plurality of temperatures based on the reaction rate equation from the remaining functional group ratio 2, a fitting step of calculating an activation energy Ea1 and a frequency factor A1 from the reaction rate constant 1 at the plurality of temperatures using an Arrhenius plot, and calculating an activation energy Ea2 and a frequency factor A2 from the reaction rate constant 2 at the plurality of temperatures using an Arrhenius plot, a polymerization catalyst selecting step of determining whether the polymerization catalyst satisfies following Condition 1 based on the activation energies Ea1 and Ea2 or not, Average value of $-Ea1/R$ and $-Ea2/R$ is $-7100$ or more and $-2900$ or less    [Condition 1]

(R: gas constant (8.314 J/mol/K)), an approximation equation setting step of, when the polymerization catalyst is determined to satisfy Condition 1 in the polymerization catalyst selecting step, setting an approximation equation a from two amounts of the polymerization catalyst and the frequency factor A1 and the frequency factor A2 in the two catalyst amounts, ln $A=ax+b$    Approximation equation a:

A: Frequency factor
a: Constant determined by the polymerization catalyst
b: Constant determined from two catalyst amounts and frequency factor A1 and frequency factor A2
x: Added amount of polymerization catalyst to be calculated (ppm), and a catalyst addition range setting step of setting an addition range with respect to the polymerization-reactive compound with a value obtained by multiplying a constant b in the approximation equation a by 1.003 or 1.2 set as the ln A, and each calculated polymerization catalyst added amount x set as a lower limit value and an upper limit value.

[2] The method for setting conditions for use of a polymerization catalyst according to [1], in which the catalyst addition range setting step includes a step in which a combination of n kinds (n is an integer of two or more) is selected from the polymerization catalysts, an added amount $x_1$ to an added amount $x_n$ of the n kinds of polymerization catalysts are calculated to satisfy the following condition, and addition ranges of each of the polymerization catalysts are set.

$1.0035 \leq \{[(a_1 \times x_1 + b_1)/b_1] + [(a_2 \times x_2 + b_2)/b_2] + \ldots + [(a_n \times x_n + b_n)/b_n]\} - (n-1) \leq 1.2$    [Condition]

$a_1$ to $a_n$: Constants determined from n kinds of polymerization catalysts, respectively
$b_1$ to $b_n$: Constants determined from two catalyst amounts and frequency factor A1 and frequency factor A2, for respective n kinds of polymerization catalysts
$x_1$ to $x_n$: Added amounts of respective n kinds of polymerization catalysts to be calculated (ppm).

[3] The method for setting conditions for use of a polymerization catalyst according to [1] or [2], in which the physical property values 1a and 1b and the physical property values 2a and 2b are a heat value, a specific gravity, a weight-average molecular weight, a number-average molecular weight, a spectral intensity in IR measurement, a $^1$H-NMR spectral intensity, or a $^{13}$C-NMR spectral intensity.

[4] The method for setting conditions for use of a polymerization catalyst according to any one of [1] to [3], in which the polymerization catalyst is selected from a tertiary amine compound and an organic tin compound.

[5] The method for setting conditions for use of a polymerization catalyst according to any one of [1] to [4], in which the polymerization catalyst is selected from 2,4,6-collidine, N,N-dimethylbenzylamine, 3,5-lutidine, dimethyltin dichloride, and dibutyltin dichloride.

[6] The method for setting conditions for use of a polymerization catalyst according to any one of [1] to [5], in which the polymerization-reactive compound is a polyisocyanate compound and an active hydrogen compound.

[7] The method for setting conditions for use of a polymerization catalyst according to [6], in which the polyisocyanate compound is at least one selected from aliphatic polyisocyanate, aromatic polyisocyanate, heterocyclic polyisocyanate, and alicyclic polyisocyanate, and the active hydrogen compound is at least one selected from the group consisting of a polythiol compound having two or more mercapto groups, a hydroxythiol compound having one or more mercapto groups and one or more hydroxyl groups, a polyol compound having two or more hydroxyl groups, and an amine compound.

[8] The method for setting conditions for use of a polymerization catalyst according to any one of [1] to [5], in which the polymerization-reactive compound is at least one compound selected from an allyl carbonate compound, a (meth)acrylate compound, and an episulfide compound.

[9] The method for setting conditions for use of a polymerization catalyst according to [8], in which the allyl carbonate compound is represented by General Formula (1),

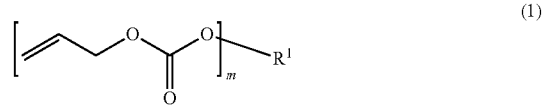

(1)

in which $R^1$ represents a divalent to 20-valent group derived from a chained or branched aliphatic polyol with 3 to 35 carbon atoms which may include a hetero atom, or a divalent to 20-valent group derived from a cyclic aliphatic polyol with 5 to 40 carbon atoms which may include a hetero atom, m represents an integer of 2 to 10, and $R^1$ does not include an allyloxycarbonyl group.

[10] The method for setting conditions for use of a polymerization catalyst according to [8], in which the (meth)acrylate compound is represented by General Formula (2),

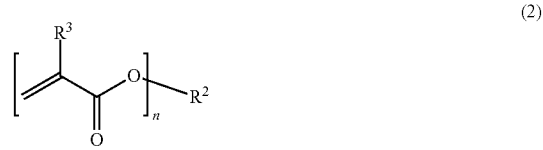

(2)

in which $R^2$ represents a divalent to tetravalent organic group with 1 to 30 carbon atoms which may include a hetero atom or an aromatic group, $R^3$ represents a hydrogen atom or a methyl group, and n represents an integer of 2 to 4.

[11] The method for setting conditions for use of a polymerization catalyst according to [8], in which the episulfide compound is represented by General Formula (3),

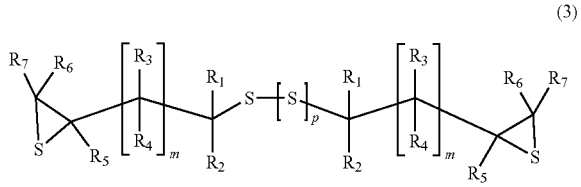 (3)

in which in General Formula (3), $R_1$ to $R_7$ may be the same or different and represent a hydrogen atom, a linear or branched alkyl group with 1 or more and 10 or fewer carbon atoms, or a substituted or unsubstituted aryl group with 6 or more and 18 or fewer carbon atoms, m represents an integer of 0 or more and 2 or less, and p represents an integer of 0 or more and 4 or less.

[12] A polymerization condition setting method including a polymerization catalyst amount determining step of determining an added amount y of a polymerization catalyst from a kind and an addition range of a polymerization catalyst with respect to a desired polymerizable compound set by the method according to any one of [1] to [11], a reaction rate constant calculating step of calculating a reaction rate constant for each of a plurality of reaction temperatures T at the added amount y of the polymerization catalyst in Equation b derived from the approximation equation a and an Arrhenius equation, $$k = \text{Exp}[(-Ea/R) \times (1/T) + (ay+b)]$$ Equation b:

k: Reaction rate constant
-Ea/R: Value included in -7100 or more and -2900 or less, calculated in the polymerization catalyst selecting step
T: Desired reaction temperature (K)
a: Constant determined by the polymerization catalyst
b: Constant determined from two catalyst amounts and frequency factor A1 and frequency factor A2
y: Added amount of polymerization catalyst determined in the polymerization catalyst amount determining step (ppm), and
a polymerization program calculating step of back-calculating a polymerization temperature for each predetermined time in a polymerization time based on the reaction rate equation using the reaction rate constant, to satisfy the following conditions,
(Conditions)
an average polymerization rate from a 10% polymerization ratio point to an 80% polymerization ratio point is selected and determined in a range of 0.4%/hr or more and 15%/hr or less, a plurality of polymerization rates are calculated at every predetermined time in a time when a polymerization ratio is 10% or more and 80% or less, standard deviation, which is a positive square root of a dispersion of the plurality of polymerization rates and the average polymerization rate, is calculated, and the calculated standard deviation is 2.3%/hr or less.

[13] The polymerization condition setting method according to [12], in which the polymerization catalyst amount determining step includes a step of determining n kinds (n is an integer of two or more) of polymerization catalyst kinds and an added amount $y_1$ to an added amount $y_n$ for the respective polymerization catalyst kinds, the reaction rate constant calculating step includes a step in which, in Equation b derived from the approximation equation a and an Arrhenius equation, a reaction rate constant $k_1$ to a reaction rate constant $k_n$ are calculated for each of a plurality of reaction temperatures T at each of added amount $y_1$ to added amount $y_n$ of n kinds of polymerization catalysts, and a reaction rate constant $k_\Sigma$ is calculated for each of the plurality of reaction temperatures T when using n kinds of polymerization catalysts in combination, using equation c, $$k_i = \text{Exp}[(-Ea/R) \times (1/T) + (a_i x_i + b_i)]$$ Equation b:

$k_i$: Reaction rate constants $k_1$ to $k_n$
-Ea/R: Value included in -7100 or more and -2900 or less, calculated in the polymerization catalyst selecting step
T: Desired reaction temperature (K)
$a_i$: Constant determined by respective n kinds of polymerization catalysts
$b_i$: Constant determined from two catalyst amounts and frequency factor A1 and frequency factor A2 in each of n kinds of polymerization catalysts
$x_i$: Added amounts $y_1$ to $y_n$ of each of n kinds of polymerization catalysts (ppm) determined by polymerization catalyst amount determining step $$k_\Sigma = \Sigma_{i=1}^{n} k_i$$ Equation c:

n: Integer of 2 or more, and
the polymerization program calculating step includes a step of back-calculating a polymerization temperature for each predetermined time in a polymerization time based on a reaction rate equation using the reaction rate constant $k_\Sigma$ so as to satisfy the conditions.

[14] A method for manufacturing an optical material, the method including a step of preparing a polymerizable composition by mixing a polymerizable compound and the polymerization catalyst kind in an added amount set by the method according to [12] or [13],
a step of introducing the polymerizable composition into a mold, and
a step of polymerizing and curing the polymerizable composition so as to satisfy polymerization temperature conditions for each polymerization time calculated in [12] or [13].

[15] A polymerization catalyst use condition setting apparatus including a physical property acquiring unit for, when a composition 1 including a polymerization-reactive compound and a predetermined amount of a polymerization catalyst is heated and maintained at a plurality of temperatures, acquiring a physical property value 1a derived from functional groups of the polymerization-reactive compound before heating and a physical property value 1b derived from remaining functional groups after maintaining a temperature for a predetermined time, and, when a composition 2, which is different from the composition 1 only in an amount of the polymerization catalyst, is heated and maintained at the plurality of temperatures, acquiring a physical property value 2a derived from functional groups of the polymerization-reactive compound before heating and a physical property value 2b derived from remaining functional groups after maintaining a temperature for a predetermined time,
a remaining functional group ratio calculating unit which calculates a remaining functional group ratio 1 at the plurality of temperatures from the physical property value 1a and physical property value 1b, and calculates a remaining functional group ratio 2 at the plurality of temperatures from the physical property value 2a and physical property value 2b,
a reaction rate constant calculating unit which calculates a reaction rate constant 1 at the plurality of temperatures based on a reaction rate equation from the remaining functional group ratio 1, and calculates a reaction rate constant 2 at the plurality of temperatures based on the reaction rate equation from the remaining functional group ratio 2, a fitting unit which calculates an activation energy Ea1 and a frequency factor A1 from the reaction rate constant 1 at the plurality of temperatures using an Arrhenius plot, and calculates an activation energy Ea2 and a frequency factor A2 from the reaction rate constant 2 at the plurality of temperatures using an Arrhenius plot, a polymerization catalyst selecting unit which determines whether the polymerization catalyst satisfies following Condition 1 based on the activation energies Ea1 and Ea2 or not, Average value of $-Ea1/R$ and $-Ea2/R$ is $-7100$ or more and $-2900$ or less [Condition 1]

(R: gas constant (8.314 J/mol/K)), an approximation equation setting unit for, when the polymerization catalyst is determined to satisfy Condition 1 in the polymerization catalyst selecting unit, setting an approximation equation a from two amounts of the polymerization catalyst and the frequency factor A1 and the frequency factor A2 in the two catalyst amounts, $\ln A = ax + b$  Approximation equation a:

A: Frequency factor
a: Constant determined by the polymerization catalyst
b: Constant determined from two catalyst amounts and frequency factor A1 and frequency factor A2
x: Added amount of polymerization catalyst to be calculated (ppm), and a catalyst addition range setting unit which sets an addition range with a value obtained by multiplying a constant b in the approximation equation a by 1.003 or 1.2 set as the ln A, and each calculated polymerization catalyst added amount x set as a lower limit value and an upper limit value.

[16] A polymerization condition setting apparatus including the setting apparatus according to [15] for setting a kind of polymerization catalyst and an addition range with respect to a desired polymerizable compound, a polymerization catalyst amount determining unit which determines an added amount y of the polymerization catalyst from the kind and addition range of the polymerization catalyst with respect to the desired polymerizable compound set in the setting apparatus, a reaction rate constant calculating unit which calculates a reaction rate constant for each of a plurality of reaction temperatures T at the added amount y of the polymerization catalyst in Equation b derived from the approximation equation a and an Arrhenius equation, $k = \mathrm{Exp}[(-Ea/R) \times (1/T) + (ay+b)]$  Equation b:

k: Reaction rate constant
$-Ea/R$: Value included in $-7100$ or more and $-2900$ or less, calculated in the polymerization catalyst selecting step
T: Desired reaction temperature (K)
a: Constant determined by the polymerization catalyst
b: Constant determined from two catalyst amounts and frequency factor A1 and frequency factor A2
y: Added amount of polymerization catalyst determined in the polymerization catalyst amount determining step (ppm), and a polymerization program calculating unit which back-calculates a polymerization temperature for each predetermined time in a polymerization time based on the reaction rate equation using the reaction rate constant, to satisfy the following conditions, (Conditions)
an average polymerization rate from a 10% polymerization ratio point to an 80% polymerization ratio point is selected and determined in a range of 0.4%/hr or more and 15%/hr or less,
a plurality of polymerization rates are calculated at every predetermined time in a time when a polymerization ratio is 10% or more and 80% or less,
standard deviation, which is a positive square root of a dispersion of the plurality of polymerization rates and the average polymerization rate, is calculated, and
the calculated standard deviation is 2.3%/hr or less.

[17] An optical material manufacturing apparatus including the setting apparatus according to [15] which sets a kind and an addition range of a polymerization catalyst with respect to a desired polymerizable compound, the polymerization condition setting apparatus according to [16], which calculates a polymerization program from the kind and addition range of the polymerization catalyst with respect to the desired polymerizable compound set in the setting apparatus, a heating unit which heats a composition including the desired polymerization-reactive compound and a predetermined amount of the polymerization catalyst, and a control unit which controls the heating unit to heat the composition including the polymerization-reactive compound and the polymerization catalyst, based on the polymerization program obtained by the polymerization condition setting apparatus.

[18] A computer program for setting use conditions for a polymerization catalyst to be used for polymerizing a polymerization-reactive compound, the program causing a computer to implement functions of:

a physical property acquiring means for, when a composition 1 including a polymerization-reactive compound and a predetermined amount of a polymerization catalyst is heated and maintained at a plurality of temperatures, acquiring a physical property value 1a derived from functional groups of the polymerization-reactive compound before heating and a physical property value 1b derived from remaining functional groups after maintaining a temperature for a predetermined time, and, when a composition 2, which is different from the composition 1 only in an amount of the polymerization catalyst, is heated and maintained at the plurality of temperatures, acquiring a physical property value 2a derived from functional groups of the polymerization-reactive compound before heating and a physical property value 2b derived from remaining functional groups after maintaining a temperature for a predetermined time, a remaining functional group ratio calculating means for calculating a remaining functional group ratio 1 at the plurality of temperatures from the physical property value 1a and physical property value 1b, and calculating a remaining functional group ratio 2 at the plurality of temperatures from the physical property value 2a and physical property value 2b, a reaction rate constant calculating means for calculating a reaction rate constant 1 at the plurality of temperatures based on a reaction rate equation from the remaining functional group ratio 1, and calculating a reaction rate constant 2 at the plurality of temperatures based on the reaction rate equation from the remaining functional group ratio 2, a fitting means for calculating an activation energy Ea1 and a frequency factor A1 from the reaction rate constant 1 at the plurality of temperatures using an Arrhenius plot, and calculating an activation energy Ea2 and a frequency factor A2 from the reaction rate constant 2 at the plurality of temperatures using an Arrhenius plot, a polymerization catalyst selecting means for determining whether the polymerization catalyst satisfies following Condition 1 based on the activation energies Ea1 and Ea2 or not, Average value of $-Ea1/R$ and $-Ea2/R$ is $-7100$ or more and $-2900$ or less [Condition 1]

(R: gas constant (8.314 J/mol/K)), an approximation equation setting means for, when the polymerization catalyst is determined to satisfy Condition 1 in the polymerization catalyst selecting step, setting an approximation equation a from two amounts of the polymerization catalyst and the frequency factor A1 and the frequency factor A2 in the two catalyst amounts, ln $A=ax+b$   Approximation equation a:

A: Frequency factor
a: Constant determined by the polymerization catalyst
b: Constant determined from two catalyst amounts and frequency factor A1 and frequency factor A2
x: Added amount of polymerization catalyst to be calculated (ppm), and a catalyst addition range setting means for setting an addition range with a value obtained by multiplying a constant b in the approximation equation a by 1.003 or 1.2 set as the ln A, and each calculated polymerization catalyst added amount x set as a lower limit value and an upper limit value.

[19] A computer program for setting polymerization conditions in a composition including a polymerization-reactive compound and a polymerization catalyst, the program causing a computer to implement functions of:

each of the means according to [18], a polymerization catalyst amount determining means for determining an added amount y of a polymerization catalyst from the kind and addition range of the polymerization catalyst with respect to the desired polymerizable compound set in the catalyst addition range setting means, a reaction rate constant calculating means for calculating a reaction rate constant for each of a plurality of reaction temperatures T at the added amount y of a polymerization catalyst in Equation b derived from the approximation equation a and an Arrhenius equation, $k=\text{Exp}[(-Ea/R)\times(1/T)+(ay+b)]$   Equation b:

k: Reaction rate constant
$-Ea/R$: Value included in $-7100$ or more and $-2900$ or less, calculated in the polymerization catalyst selecting step
T: Desired reaction temperature (K)
a: Constant determined by the polymerization catalyst
b: Constant determined from two catalyst amounts and frequency factor A1 and frequency factor A2
y: Added amount of polymerization catalyst determined in the polymerization catalyst amount determining step (ppm), and a polymerization program calculating means for back-calculating a polymerization temperature for each predetermined time in a polymerization time based on a reaction rate equation using the reaction rate constant, to satisfy the following conditions, (Conditions)

an average polymerization rate from a 10% polymerization ratio point to an 80% polymerization ratio point is selected and determined in a range of 0.4%/hr or more and 15%/hr or less, a plurality of polymerization rates are calculated at every predetermined time in a time when a polymerization ratio is 10% or more and 80% or less, standard deviation, which is a positive square root of a dispersion of the plurality of polymerization rates and the average polymerization rate, is calculated, and the calculated standard deviation is 2.3%/hr or less.

In the present invention, "remaining functional group" means a functional group which remains unconsumed by the reaction among the functional groups involved in the polymerization reaction.

In addition, in the present invention, "polymerization catalyst" means a thermal polymerization catalyst and/or a thermal polymerization initiator or a photopolymerization initiator.

Advantageous Effects of Invention

According to the present invention, it is possible to determine a kind and addition range of a polymerization catalyst which is able to obtain an optical material having an excellent appearance, in which the generation of optical distortion and striae is suppressed, and to set conditions for a polymerization program or the like. Furthermore, including the set polymerization catalyst kind within the above range makes it possible to obtain an optical material having an excellent appearance, in which the generation of optical distortion and striae is suppressed.

In addition, according to the present invention, it is possible to provide a polymerization condition setting apparatus and a computer program for setting use conditions for a polymerization catalyst, and an optical material manufacturing apparatus provided with the polymerization condition setting apparatus.

DESCRIPTION OF EMBODIMENTS

Figure 1:
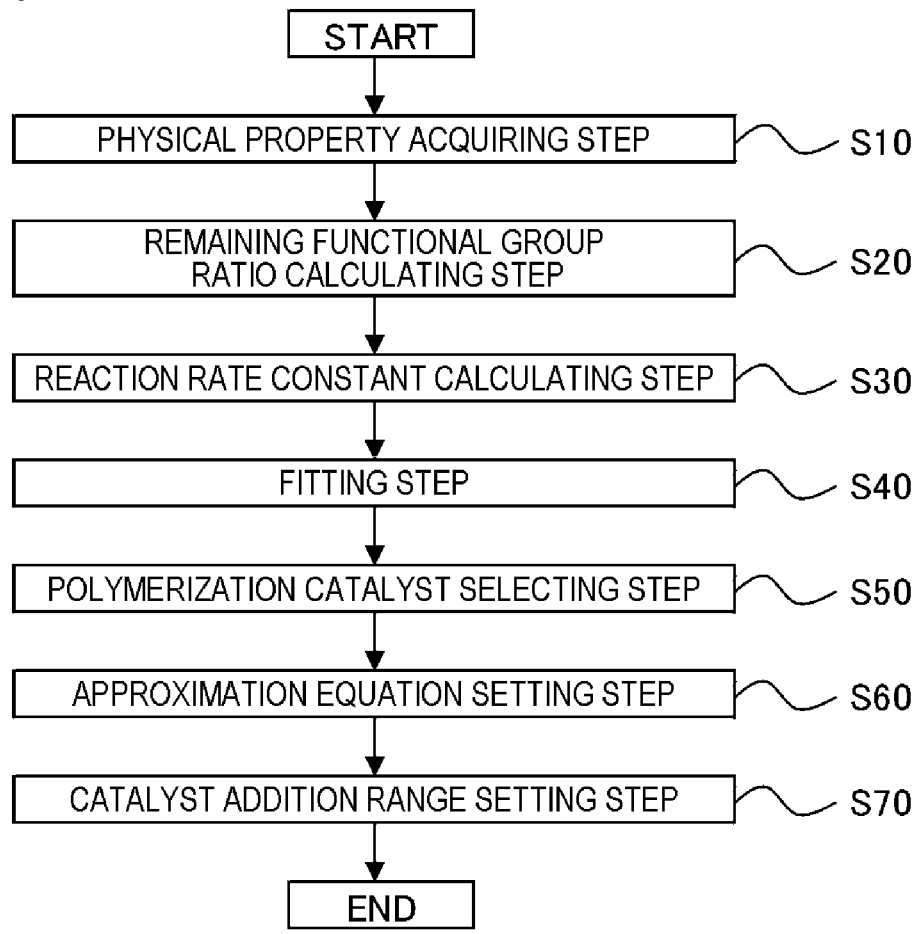
FIG. 1 is a flow chart of a method for setting conditions for use of a polymerization catalyst according to the present embodiment.

A description will be given below of embodiments of the present invention using drawings. In all the drawings, the same components are denoted by the same reference numerals and description thereof will not be repeated, as appropriate.

[Method for Setting Conditions for Use of Polymerization Catalyst and Setting Apparatus]

In the following description, in a polymerization catalyst use condition setting apparatus 1 (below, "setting apparatus 1"), a storage unit 2, a physical property acquiring unit 10, a remaining functional group ratio calculating unit 20, a reaction rate constant calculating unit 30, a fitting unit 40, a polymerization catalyst selecting unit 50, an approximation equation setting unit 60, and catalyst addition range setting unit 70 are not shown in a configuration of hardware units, but as blocks of functional units. In the polymerization catalyst use condition setting apparatus 1, the storage unit 2, the physical property acquiring unit 10, the remaining functional group ratio calculating unit 20, the reaction rate constant calculating unit 30, the fitting unit 40, the polymerization catalyst selecting unit 50, the approximation equation setting unit 60, and the catalyst addition range setting unit 70 are implemented by any combination of hardware and software, centering on a CPU of any computer, a memory, a computer program which implements components of a figure loaded in a memory, storage media such as a hard disk which stores the program, or a network connection interface. Then, there are various modifications of the implementation method and apparatuses.

FIG. 1 is a flow chart of a method for setting conditions for use of a polymerization catalyst according to the present embodiment (also referred to below as a setting method).

The method for setting conditions for use of a polymerization catalyst according to the present embodiment is a method for setting conditions for use of a polymerization catalyst in a composition including a polymerization-reactive compound.

As shown in FIG. 1, the setting method of the present embodiment includes a physical property acquiring step S10, a remaining functional group ratio calculating step S20, a reaction rate constant calculating step S30, a fitting step S40, a polymerization catalyst selecting step S50, an approximation equation setting step S60, and a catalyst addition range setting step S70.

In the physical property acquiring step S10, in a case where a composition 1 including the polymerization-reactive compound and a predetermined amount of the polymerization catalyst is heated and maintained at a plurality of temperatures, a physical property value 1a derived from the functional groups of the polymerization-reactive compound before heating and a physical property value 1b derived from the remaining functional groups after maintaining a temperature for a predetermined time are acquired, and, in a case where a composition 2, which is different from the composition 1 only in an amount of the polymerization catalyst, is heated and maintained at a plurality of temperatures, a physical property value 2a derived from the functional groups of the polymerization-reactive compound before heating and a physical property value 2b derived from the remaining functional groups after maintaining a temperature for a predetermined time are acquired.

In the remaining functional group ratio calculating step S20, a remaining functional group ratio 1 is calculated at the plurality of temperatures from the physical property value 1a and physical property value 1b, and a remaining functional group ratio 2 is calculated at the plurality of temperatures from the physical property value 2a and physical property value 2b.

In the reaction rate constant calculating step S30, a reaction rate constant 1 is calculated at the plurality of temperatures based on a reaction rate equation from the remaining functional group ratio 1, and a reaction rate constant 2 is calculated at the plurality of temperatures based on the reaction rate equation from the remaining functional group ratio 2.

In the fitting step S40, an activation energy Ea1 and a frequency factor A1 are calculated from the reaction rate constant 1 at the plurality of temperatures using an Arrhenius plot, and an activation energy Ea2 and a frequency factor A2 are calculated from the reaction rate constant 2 at the plurality of temperatures using an Arrhenius plot.

In the polymerization catalyst selecting step S50, it is determined whether the polymerization catalyst satisfies following Condition 1 based on the activation energies Ea1 and Ea2 or not.

Average value of $-Ea1/R$ and $-Ea2/R$ is $-7100$ or more and $-2900$ or less. [Condition 1]

(R: gas constant (8.314 J/mol/K))

In the approximation equation setting step S60, in a case where the polymerization catalyst is determined to satisfy Condition 1 in the polymerization catalyst selecting step S50, an approximation equation a is set from two amounts of the polymerization catalyst and the frequency factor A1 and the frequency factor A2 in the two catalyst amounts.

Approximation equation a: $\ln A = ax + b$

A: Frequency factor
a: Constant determined by the polymerization catalyst
b: Constant determined from two catalyst amounts and frequency factor A1 and frequency factor A2
x: Added amount of polymerization catalyst to be calculated (ppm)

In the catalyst addition range setting step S70, an addition range with respect to the polymerization-reactive compound is set with a value obtained by multiplying a constant b in the approximation equation a by 1.003 or 1.2 set as the ln A, and each calculated polymerization catalyst added amount x set as a lower limit value and an upper limit value.

A description will be given below of the polymerization-reactive compound, the polymerization catalyst, and the composition including the above, as used in the present embodiment.

It is possible to use a polymerization-reactive compound appropriately selected from polymerization-reactive compounds known in the related art in a range in which it is possible to obtain the effect of the present invention. Examples of polymerization-reactive compounds include a polyiso(thio)cyanate compound having two or more isocyanato groups or isothiocyanato groups, a (thio)epoxide compound having one or more epoxy groups or thioepoxy groups, an oxetanyl compound having one or more oxetanyl groups, a thietanyl compound having one or more thietanyl groups or having an oxetanyl group and a thietanyl group, (meth)acrylate compounds, a (meth)acryloyl compound having one or more methacryloyloxy group, acryloyloxy group, methacryloylthio group, acryloylthio group, methacrylamide group, or acrylamide group, an alkene compound having one or more polymerizable carbon-carbon double bond group other than a methacryloyloxy group, an acryloyloxy group, a methacryloylthio group, an acryloylthio group, a methacrylamide group, or an acrylamide group, an alkyne compound having one or more polymerizable carbon-carbon triple bond group, a bifunctional or higher active hydrogen compound, an acid anhydride having one or more acid anhydride group, an allyl carbonate compound, and the like and it is possible to use one kind or two or more kinds selected from the above.

The active hydrogen compound and acid anhydride are used in combination with another polymerizable compound.

Examples of polyiso(thio)cyanate compounds include the compounds described in International Publication No. 2018/070383. In the present embodiment, the isocyanate compound (A) preferably includes at least one kind selected from xylylene diisocyanate, phenylene diisocyanate, tolylene diisocyanate, diphenylmethane diisocyanate, 2,5-bis(isocyanatomethyl)bicyclo-[2.2.1]-heptane, 2,6-bis(isocyanatomethyl)bicyclo-[2.2.1]-heptane, hexamethylene diisocyanate, pentamethylene diisocyanate, isophorone diisocyanate, bis(isocyanatomethyl)cyclohexane, and dicyclohexylmethane diisocyanate, and more preferably includes at least one kind selected from xylylene diisocyanate, phenylene diisocyanate, tolylene diisocyanate, diphenylmethane diisocyanate, 2,5-bis(isocyanatomethyl)bicyclo-[2.2.1]-heptane, and 2,6-bis(isocyanatomethyl)bicyclo-[2.2.1]-heptane.

Examples of (thio)epoxide compounds include the compounds described in International Publication No. 2018/070383.

Examples of thio-epoxide compounds (also called episulfide compounds) include the compounds described as polyepithio compounds in International Publication No. 2015/037628.

As the episulfide compound, it is preferable to use a compound represented by General Formula (3).

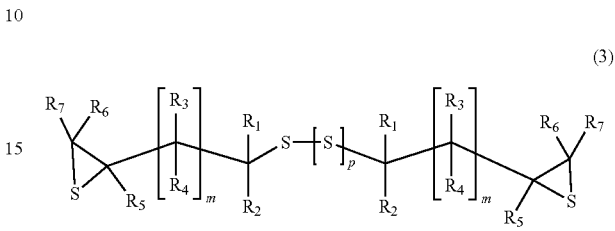

(3)

In General Formula (3), $R_1$ to $R_7$ may be the same or different and represent a hydrogen atom, a linear or branched alkyl group with 1 or more and 10 or fewer carbon atoms, or a substituted or unsubstituted aryl group with 6 or more and 18 or fewer carbon atoms. $R_1$ to $R_7$ may be the same or different.

Examples of the linear or branched alkyl group with 1 or more and 10 or fewer carbon atoms include a methyl group, an ethyl group, an n-propyl group, an isopropyl group, an n-butyl group, a sec-butyl group, a tert-butyl group, a pentyl group, a hexyl group, a heptyl group, an octyl group, a nonyl group, a decyl group, and the like. Examples of the aryl group include aryl groups with 6 or more and 18 or fewer carbon atoms such as phenyl, tolyl, xylyl, biphenyl, naphthyl, anthryl, and phenanthryl.

Examples of the substituent of the substituted aryl group include an alkyl group with 1 or more and 10 or fewer carbon atoms, a halogen atom, a hydroxyl group, an alkoxyl group or an alkylthio group with 1 or more and 10 or fewer carbon atoms, an amino group, or the like.

$R_1$ to $R_7$ may be the same or different and are preferably a hydrogen atom or a linear or branched alkyl group with 1 or more and 10 or fewer carbon atoms, and all are preferably hydrogen atoms.

m represents an integer of 0 or more and 2 or less, preferably 0 or 1, and more preferably 0. p represents an integer of 0 or more and 4 or less.

Examples of oxetanyl compounds or thietanyl compounds include the compounds described in International Publication No. 2018/070383.

It is possible to represent the (meth)acrylate compound by the following formula.

(2)

$R^2$ represents a divalent to tetravalent organic group with 1 to 30 carbon atoms which may include a hetero atom or an aromatic group. $R^3$ represents a hydrogen atom or a methyl group. n represents an integer of 2 to 4.

In addition, examples of the (meth)acrylate compound (B) include compounds represented by General Formula (2-1) and General Formula (2-2).

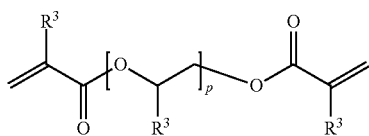

(2-1)

p represents a numerical value of 1 to 100 and $R^3$ represents a hydrogen atom or a methyl group, and may not be the same. p is preferably a numerical value of 1 to 50, more preferably a numerical value of 1 to 20, even more preferably a numerical value of 2 to 10, and particularly preferably a numerical value of 2 to 4.

Examples of the (meth)acrylate compound represented by General Formula (2-1) include at least one kind selected from ethylene glycol dimethacrylate, diethylene glycol dimethacrylate, triethylene glycol dimethacrylate, tetraethylene glycol dimethacrylate, ethylene glycol diacrylate, diethylene glycol diacrylate, triethylene glycol diacrylate, tetraethylene glycol diacrylate, propylene glycol dimethacrylate, dipropylene glycol dimethacrylate, tripropylene glycol dimethacrylate, tetrapropylene glycol dimethacrylate, propylene glycol diacrylate, dipropylene glycol diacrylate, tripropylene glycol diacrylate, and tetrapropylene glycol diacrylate.

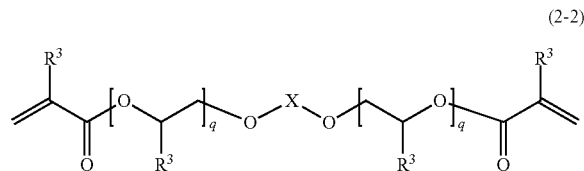

(2-2)

q each represents a numerical value of 1 or more, and the sum of two q's represents a numerical value of 2 to 100. $R^3$ represents a hydrogen atom or a methyl group, and may not be the same. X represents a substituted or unsubstituted divalent aromatic group or a substituted or unsubstituted divalent aliphatic group, which may include an aromatic group with 1 to 20 carbon atoms.

Examples of the (meth)acrylate compound represented by General Formula (2-2) include at least one kind selected from bisphenol A dimethacrylate, methylene-bis-(4,1-phenylene)-bis-(2-methacrylate), bisphenol A diacrylate, methylene-bis-(4,1-phenylene)-bis-(2-acrylate), 2,2-bis-(4-methacryloyloxyphenyl) propane, 2,2-bis-(4-acryloyloxyphenyl) propane, 2-(4-methacryloyloxyphenyl)-2-(4-methacryloyloxyethoxyphenyl) pro pane, 2-(4-acryloyloxyphenyl)-2-(4-acryloyloxyethoxyphenyl) propane, 2,2-bis-(4-methacryloyloxyethoxyphenyl) propane, 2,2-bis-(4-acryloyloxyethoxyphenyl) propane, 2-(4-methacryloyloxyethoxyphenyl)-2-(4-(methacryloyloxyethoxy) ethoxyphenyl) propane, 2-(4-acryloyloxyethoxyphenyl)-2-(4-(acryloyloxyethoxy) ethoxyphenyl) propane, 2,2-bis-(4-(methacryloyloxyethoxy)ethoxyphenyl)propane, and 2,2-bis-(4-(acryloyloxyethoxy)ethoxyphenyl)propane.

Examples of (meth)acrylate compounds other than the above include at least one kind selected from the group consisting of butanediol dimethacrylate, hexamethylene dimethacrylate, 2,2-bis(4-methacryloyloxyethoxy-3,5-dibromophenyl)propane, 2,2-bis-(4-methacryloyloxypentaethoxyphenyl)propane, pentaerythritol triacrylate, pentaerythritol tetraacrylate, trimethylolpropane triacrylate, dipentaerythritol hexaacrylate, bisphenol A-diglycidyl ether diacrylate-based, bisphenol A-diglycidyl ether dimethacrylate-based, tetrabromobisphenol A-diglycidyl ether diacrylate-based, and tetrabromobisphenol A-diglycidyl ether dimethacrylate.

Among these exemplified compounds, the (meth)acrylate compound (B) is preferably at least one kind selected from diethylene glycol dimethacrylate, triethylene glycol dimethacrylate, diethylene glycol diacrylate, triethylene glycol diacrylate, dipropylene glycol dimethacrylate, tripropylene glycol dimethacrylate, dipropylene glycol diacrylate, and tripropylene glycol diacrylate, more preferably at least one kind selected from diethylene glycol dimethacrylate, triethylene glycol dimethacrylate, diethylene glycol diacrylate, and triethylene glycol diacrylate, and even more preferably at least one kind selected from diethylene glycol dimethacrylate and triethylene glycol dimethacrylate.

Examples of alkene compounds or alkyne compounds include the compounds described in International Publication No. 2018/070383.

Examples of bifunctional or higher active hydrogen compounds include poly(thi)ol compounds having two or more hydroxy groups or mercapto groups, polyamine compounds having two or more amino groups or secondary amino groups, and polycarboxylic acid compounds having two or more carboxyl groups, and the like. In addition, examples thereof also include a compound having two or more active hydrogen groups selected from a hydroxy group, a mercapto group, an amino group, a secondary amino group, a carboxyl group and the like, in one molecule. Two or more active hydrogen groups may be the same or different. Examples of bifunctional or higher active hydrogen compounds include the compounds described in International Publication No. 2018/070383.

The active hydrogen compound is preferably a polythiol compound having two or more mercapto groups.

The polythiol compounds are preferably at least one kind selected from 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4-mercaptomethyl-1,8-dimercapto-3,6-dithiaoctane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis (mercaptomethylthio)propane, 4,6-bis (mercaptomethylthio)-1,3-dithiane, 2-(2,2-bis (mercaptomethylthio)ethyl)-1,3-dithiethane, 1,1,2,2-tetrakis (mercaptomethylthio)ethane, 3-mercaptomethyl-1,5-dimercapto-2,4-dithiapentane, tris(mercaptomethylthio) methane, and ethylene glycol bis(3-mercaptopropionate).

Examples of acid anhydrides include the compounds described in International Publication No. 2018/070383.

It is possible to represent the allyl carbonate compound by the following formula.

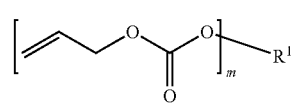

(1)

$R^1$ represents a chained or branched divalent to 20-valent group derived from an aliphatic polyol with 3 to 35 carbon atoms which may include a hetero atom, or a divalent to 20-valent group derived from a cyclic aliphatic polyol with 5 to 40 carbon atoms which may include a hetero atom. m represents an integer of 2 to 10. $R^1$ does not include an allyloxycarbonyl group.

It is possible for the allyl carbonate compound to include an oligomer thereof. The oligomer is, for example, poly(allyl carbonate) produced by a transesterification reaction between diallyl carbonate and a polyol and in which two or more molecules of a polyol are linked via a carbonate bond. The allyl carbonate compound is a poly(allyl carbonate) of a chained or branched chain aliphaticpolyol having 3 to 35 carbon atoms. A poly(allyl carbonate) of a cyclic aliphatic polyol having 5 to 40 carbon atoms in the molecule is also suitable for this purpose. These polyols usually able to have 2 to 6 hydroxyl groups in the molecule, and preferably to have 2 to 4. It is also possible to use a mixed poly(allyl carbonate), that is, a poly(allyl carbonate) derived from two or more kinds of polyols and obtainable by mixing a single polyol poly(allyl carbonate), or a poly(allyl carbonate) directly obtainable by a chemical reaction starting from a polyol mixture and diallyl carbonate. Finally, it is possible for all these poly(allyl carbonates) to take the form of monomers or mixtures of monomers and oligomers.

Specific examples of the polyol forming $R^1$ in General Formula (1) include diethylene glycol, dipropylene glycol, triethylene glycol, tetraethylene glycol, 1,3-propanediol, 1,4-butanediol, 1,5-pentanediol, 1,6-hexanediol, neopentyl glycol, 3-methyl-1,5-pentanediol, 2-methyl-2-ethyl-1,3-propanediol, 2,2-diethyl-1,3-propanediol, 2,2,4-trimethyl-1,3-pentanediol, 1,4-dimethylolcyclohexane, 4,8-bis(hydroxymethyl)-[5.2.1.0$^{2,6}$]tricyclodecane, glycerol, trimethylolpropane, tris(hydroxyethyl)isocyanurate, pentaerythritol, diglycerol, ditrimethylolpropane, dipentaerythritol, and the like.

Accordingly, examples of allyl carbonate compounds include at least one kind selected from: at least one kind of diol bis(allyl carbonate) compound selected from diethylene glycol, dipropylene glycol, triethylene glycol, tetraethylene glycol, 1,3-propanediol, 1,4-butanediol, 1,5-pentanediol, 1,6-hexanediol, neopentyl glycol, 3-methyl-1,5-pentanediol, 2-methyl-2-ethyl-1,3-propanediol, 2,2-diethyl-1,3-propanediol, 2,2,4-trimethyl-1,3-pentanediol, 1,4-dimethylolcyclohexane, and 4,8-bis(hydroxymethyl)-[5.2.1.0$^{2,6}$]tricyclodecane; at least one kind of triol tris(allyl carbonate) compound selected from glycerol, trimethylolpropane, and tris(hydroxyethyl)isocyanurate; at least one kind of tetraol tetra(allyl carbonate) compound selected from pentaerythritol, diglycerol, and ditrimethylolpropane, a hexa(allyl carbonate) compound of dipentaerythritol, and a mixed poly(allyl carbonate) compound of at least two kinds of compounds selected from the diol, the triol, the tetraol and the dipentaerythritol.

The "bis(allyl carbonate) of a mixture of at least two kinds of diols" is, for example, obtained as a mixture of the following monomer components and oligomer components in a case where the diol is diethylene glycol and neopentyl glycol.

Monomer Components
(1) Diethylene glycol bis(allyl carbonate)
(2) Neopentyl glycol bis(allyl carbonate)
Oligomer Components
(3) Oligomers including only hydrocarbon (and ether) derived from diethylene glycol
(4) Oligomers including only hydrocarbons derived from neopentyl glycol
(5) Complex oligomer including both hydrocarbon (and ether) derived from diethylene glycol and hydrocarbon derived from neopentyl glycol The following are preferable examples of allyl carbonate polymerizable compounds suitable for the purpose of the present invention.

(i) Mixture of Diethylene Glycol Bis(Allyl Carbonate) Compound and Oligomer Thereof It is possible to define the diethylene glycol bis(allyl carbonate) by Formula (1-1).

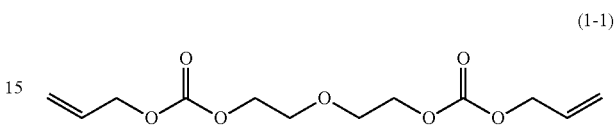

(1-1)

In addition, it is possible to define the oligomer of diethylene glycol bis(allyl carbonate) by Formula (1-2).

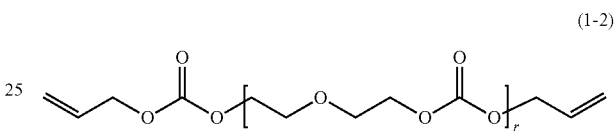

(1-2)

In the formula, r is 2 or more.

It is possible to manufacture compound (1-1) by reacting diethylene glycol bis(chloroformate) with allyl alcohol as described, for example, in "Encyclopedia of Chemical Technology", Kirk-Othmer, version III, Volume 2, pages 111-112. It is possible to easily manufacture a mixture of diethylene glycol bis(allyl carbonate) (Formula (1-1)) and an oligomer thereof (Formula (1-2)), for example, by transesterification of diallyl carbonate and diethylene glycol by operating in the presence of a basic catalyst as described in the specification of European Patent No. 35,304. These mixtures usually include up to approximately 80% by weight of oligomers.

(ii) Bis(Allyl Carbonate) Compound of Mixture of Diethylene Glycol and Neopentyl Glycol and Mixture with Oligomer Thereof This bis(allyl carbonate) compound is the same as the bis(allyl carbonate) in (i), except that diethylene glycol is substituted with a mixture of diethylene glycol and neopentyl glycol.

(iii) Poly(Allyl Carbonate) Compound of a Mixture of Diethylene Glycol and Tris(Hydroxyethyl) Isocyanurate and Mixture with Oligomer Thereof It is possible to obtain the poly(allyl carbonate) compound by transesterification of a diallyl carbonate of a mixture of diethylene glycol and tris(hydroxyethyl) isocyanurate, for example, as described in U.S. Pat. No. 4,812,545.

(iv) Poly(Allyl Carbonate) Compound of a Mixture of Diethylene Glycol and Trimethylolpropane and Mixture with Oligomer Thereof This poly(allyl carbonate) compound is the same as the poly(allyl carbonate) in (iii), except that the tris(hydroxyethyl)isocyanurate is substituted with trimethylolpropane.

(v) Poly(Allyl Carbonate) Compound of a Mixture of Diethylene Glycol and Pentaerythritol and Mixture with Oligomer Thereof This poly(allyl carbonate) compound is the same as the poly(allyl carbonate) compound in (iii) except that the tris(hydroxyethyl)isocyanurate is substituted with pentaerythritol.

(vi) Poly(Allyl Carbonate) Compound of a Mixture of Diethylene Glycol, Neopentyl Glycol, and Pentaerythritol and Mixture with Oligomer Thereof This poly(allyl carbonate) compound is the same as the poly(allyl carbonate) compound in (v) except that diethylene glycol is substituted with two kinds of diols of diethylene glycol and neopentyl glycol.

(vii) A Poly(Allyl Carbonate) Mixture Including a Mixture of a Poly(Allyl Carbonate) Compound of a Mixture of Diethylene Glycol, Neopentyl Glycol, and Pentaerythritol and an Oligomer Thereof, and a Mixture of a Bis(Allyl Carbonate) Compound of Diethylene Glycol and an Oligomer Thereof A more detailed description will be given of the cured resin forming the optical material in the present embodiment. The cured resin is obtained by heating and polymerizing a composition including a polymerization-reactive compound and a polymerization catalyst, and is preferably a cured resin obtained from a liquid composition for which a casting operation is easy and, among such cured resins, the following cured resins (a1) to (a29) are preferable.

(a1) A poly(thio)urethane resin obtained by polymerizing a polyiso(thio)cyanate compound and a poly(thi)ol compound.

In the present application, poly(thio)urethane resin means a polyurethane resin, a polythiourethane resin, or a polydithiourethane resin.

(a2) A poly(thio)urea resin obtained by polymerizing a polyisocyanate compound or a polyisothiocyanate compound and a polyamine compound In the present application, poly(thio) urea resin means polyurea resins and polythiourea resins.

(a3) A polythiourethane-polyurea resin or polydithiourethane-polyurea resin obtained by polymerizing a polyisocyanate compound or polyisothiocyanate compound with a polyamine compound and a polythiol compound (a4) A polythiourethane-polyurethane resin or polydithiourethane-polyurethane resin obtained by polymerizing a polyisocyanate compound or polyisothiocyanate compound with a polyol compound and a polythiol compound (a5) A poly(thio)epoxide resin obtained by polymerizing a (thio)epoxide compound (a6) A poly(thio)epoxide-poly(thi)ol resin obtained by polymerizing a (thio)epoxide compound and a poly(thi)ol compound (a7) A poly(thio)epoxide-polyamine resin obtained by polymerizing a (thio)epoxide compound and a polyamine compound (a8) A poly(thio)epoxide-acid anhydride resin obtained by polymerizing a (thio)epoxide compound and an acid anhydride (a9) A poly(meth)acryloyl resin obtained by polymerizing a (meth)acryloyl compound (a10) A poly(meth)acryloyl-poly(thi)ol resin obtained by polymerizing a (meth)acryloyl compound and a poly(thi)ol compound (a11) A poly(meth)acryloyl-polyalkene resin obtained by polymerizing a (meth)acryloyl compound and an alkene compound (a12) A poly(meth)acryloyl-polyalkyne resin obtained by polymerizing a (meth)acryloyl compound and an alkyne compound (a13) A poly(meth)acryloyl-polyamine resin obtained by polymerizing a (meth)acryloyl compound and a polyamine compound (a14) A poly(meth)acrylate resin obtained by polymerizing a (meth)acrylate compound (a15) A polyallyl carbonate resin obtained by polymerizing an allyl carbonate compound (a16) A poly(meth)acrylate-allyl carbonate resin obtained by polymerizing a (meth)acrylate compound and allyl carbonate compound (a17) A polyalkene resin obtained by polymerizing an alkene compound (a18) A polyalkene-poly(thi)ol resin obtained by polymerizing an alkene compound and a poly(thi)ol compound (a19) A polyalkene-polyamine resin obtained by polymerizing an alkene compound and a polyamine compound (a20) A polyalkyne resin obtained by polymerizing an alkyne compound (a21) A polyalkyne-poly(thi)ol resin obtained by polymerizing an alkyne compound and a poly(thi)ol compound (a22) A polyalkyne-polyamine resin obtained by polymerizing an alkyne compound and a polyamine compound (a23) A polyalkyne-polyalkene resin obtained by polymerizing an alkyne compound and an alkene compound (a24) A polyoxetanyl resin obtained by polymerizing an oxetanyl compound (a25) A polyoxetanyl-poly(thi)ol resin obtained by polymerizing an oxetanyl compound and a poly(thi)ol compound (a26) A polyoxetanyl-polyamine resin obtained by polymerizing an oxetanyl compound and a polyamine compound (a27) A polyoxetanyl-acid anhydride resin obtained by polymerizing an oxetanyl compound and an acid anhydride (a28) A polythietanyl-poly(thi)ol resin obtained by polymerizing a thietanyl compound and a poly(thi)ol compound (a29) A polythietanyl-polyamine resin obtained by polymerizing a thietanyl compound and a polyamine compound (a30) A polythietanyl-acid anhydride resin obtained by polymerizing a thietanyl compound and an acid anhydride (a31) A mixed resin obtained by copolymerizing two or more kinds selected from (a1) to (a30)

Among the cured resins described above in (a1) to (a31), examples of more preferable cured resins include the resins described in (a1) to (a4), (a6), and (a14) to (a16), and mixed resins thereof (mixtures of a copolymer and a resin).

In the process of manufacturing a molded article by cast polymerization of the composition in the present embodiment, in a case of curing by heat, a thermal polymerization catalyst and/or a thermal polymerization initiator is added as a polymerization catalyst, and in a case of curing by radiation other than infrared rays (heat) such as ultraviolet rays, a photopolymerization initiator is added as a polymerization catalyst.

The thermal polymerization catalyst is appropriately selected from thermal polymerization catalysts known in the related art in a range in which the effect of the present invention is able to be obtained. Examples of thermal polymerization catalysts include Lewis acids, amine compounds, tertiary amine compounds and inorganic or organic acid salts thereof, organic tin compounds, quaternary ammonium salts, organic sulfonic acids, and the like.

In the present embodiment, it is preferable to use a tertiary amine compound or an organic tin compound as the thermal polymerization catalyst.

Examples of tertiary amine compounds include 2,4,6-collidine (2,4,6-trimethylpyridine), N,N-dimethylbenzylamine, 3,5-lutidine (3,5-dimethylpyridine), and the like. Examples of organic tin compounds include dimethyltin dichloride, dibutyltin dichloride, dibutyltin dilaurate, and the like.

In the present embodiment, as the thermal polymerization catalyst, it is preferable to use at least one kind selected from 2,4,6-collidine (2,4,6-trimethylpyridine), N,N-dimethylbenzylamine, 3,5-lutidine (3,5-dimethylpyridine), dimethyltin dichloride, and dibutyltin dichloride.

Examples of the thermal polymerization initiator to be used include the compounds described in WO 2019/187176.

Examples of the photopolymerization initiators to be used include the compounds described in WO 2019/187176.

The composition in the present embodiment preferably has the following configuration from the viewpoint of the effects of the present invention. In a case of being simply described as a "polymerization catalyst", this description means a thermal polymerization catalyst and/or a thermal polymerization initiator or a photopolymerization initiator.

Composition (1): a composition including a polyisocyanate compound and an active hydrogen compound as polymerization-reactive compounds, and the polymerization catalyst.

Composition (2): a composition including at least one kind of compound selected from an allyl carbonate compound, a (meth)acrylate compound, or an episulfide compound as a polymerization-reactive compound, the polymerization catalyst, and, as necessary, the polymerization initiator.

In the composition (1), the polyisocyanate compound preferably includes at least one kind selected from aliphatic polyisocyanates, aromatic polyisocyanates, heterocyclic polyisocyanates, and alicyclic polyisocyanates, and the active hydrogen compound preferably includes at least one kind selected from the group consisting of polythiol compounds having two or more mercapto groups, hydroxythiol compounds having one or more mercapto groups and one or more hydroxyl groups, polyol compounds having two or more hydroxyl groups, and amine compounds.

In the composition (2), the allyl carbonate compound is preferably represented by General Formula (1), the (meth) acrylate compound is preferably represented by General Formula (2), and the episulfide compound is preferably represented by General Formula (3).

[Other Components such as Additives]

In addition, in the process of cast polymerizing the composition of the present embodiment to manufacture a molded article, an internal release agent may be added as necessary.

As the internal release agent, it is possible to use an acidic phosphate ester. Examples of acidic phosphate esters include phosphoric monoesters and phosphoric acid diesters, which may be used alone or in a combination of two or more kinds.

Examples of acidic phosphate esters include ZelecUN (manufactured by STEPAN), internal release agents for MR (manufactured by Mitsui Chemicals, Inc.), the JP series manufactured by Johoku Chemical Co., Ltd., the phosphanol series manufactured by Toho Chemical Industry Co., Ltd., the AP and DP series manufactured by Daihachi Chemical Industry Co., Ltd., and ZelecUN (manufactured by Stepan), and internal release agents for MR (manufactured by Mitsui Chemicals, Inc.) are more preferable.

In order to prevent the molded article formed of the cured resin in the present embodiment from deteriorating even when exposed to the outside for a long period of time, it is desirable to further add an ultraviolet absorber and a hindered amine light stabilizer to the composition in the present embodiment to impart weatherability thereto.

Furthermore, a light-control dye or a light-control pigment may be added for the purpose of imparting light-control properties. It is possible to use one or two or more kinds from representative light-control dyes or light-control pigments from spiropyran-based compounds, spirooxazine-based compounds, fulgide-based compounds, naphthopyran-based compounds, and bisimidazole compounds, according to the desired coloration.

To the composition of the present embodiment, various additives may be further added as necessary, such as a polymerization accelerator, an infrared absorber, a radical scavenger, an antioxidant, a polymerization inhibitor, a non-light-control pigment and dye, a binder, a dispersant, an antifoaming agent, and nanometer-sized organic or inorganic particles.

A cured resin obtained by heating and polymerizing the composition of the present embodiment and a molded article formed of the resin are manufactured by adding a polymerization-reactive compound and, as necessary, the various additives and the like described above. In addition, a polymerization-reactive compound, an additive, and the like not described in the present application may be added to the composition in the present embodiment as long as the effects of the present invention are not impaired.

A description will be given below of the method for setting conditions for use of a polymerization catalyst and the polymerization catalyst use condition setting apparatus 1 according to the present embodiment.

Figure 3:
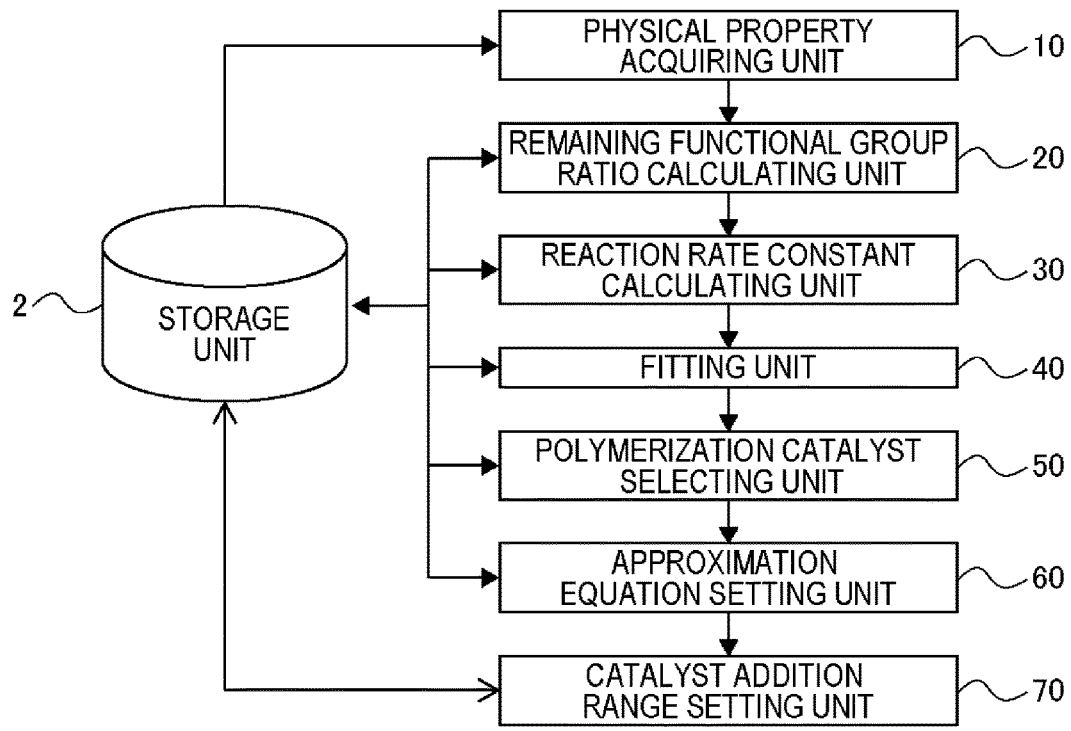
FIG. 3 is a block diagram showing a configuration of a polymerization catalyst use condition setting apparatus according to the present embodiment.

FIG. 3 is a block diagram showing the polymerization catalyst use condition setting apparatus 1 according to the present embodiment (below, the setting apparatus 1). The setting apparatus 1 according to the present embodiment is a setting apparatus which calculates the polymerization catalyst and the added amount thereof with respect to a desired polymerizable compound.

The setting apparatus 1 is provided with the physical property acquiring unit 10, the remaining functional group ratio calculating unit 20, the reaction rate constant calculating unit 30, the fitting unit 40, the polymerization catalyst selecting unit 50, the approximation equation setting unit 60, and the catalyst addition range setting unit 70.

The setting apparatus 1 is further provided with the storage unit 2. The storage unit 2 is a computer-readable medium able to record measurement results, calculation results and programs. Examples thereof include semiconductor memories, IC cards, optical discs, magnetic disks, optical magnetic disks, magnetic tapes, digital video disks, and the like. It is possible for the program recorded in the storage unit 2 to cause the computer to implement the method for setting conditions for use of a polymerization catalyst of the present embodiment.

In a case where the composition 1 including the polymerization-reactive compound and a predetermined amount of the polymerization catalyst is heated and maintained at a plurality of temperatures, the physical property acquiring unit 10 acquires the physical property value 1a derived from the functional groups of the polymerization-reactive compound before heating and the physical property value 1b derived from the remaining functional groups after maintaining a temperature for a predetermined time.

Furthermore, in a case where the composition 2, which is different from the composition 1 only in an amount of the polymerization catalyst, is heated and maintained at the plurality of temperatures, the physical property acquiring unit 10 acquires the physical property value 2a derived from the functional groups of the polymerization-reactive compound before heating and the physical property value 2b derived from the remaining functional groups after maintaining a temperature for a predetermined time.

The remaining functional group ratio calculating unit 20 calculates a remaining functional group ratio 1 at the plurality of temperatures from the physical property value 1a and physical property value 1b, and calculates a remaining functional group ratio 2 at the plurality of temperatures from the physical property value 2a and physical property value 2b.

The reaction rate constant calculating unit 30 calculates the reaction rate constant 1 at the plurality of temperatures based on a reaction rate equation from the remaining functional group ratio 1, and calculates the reaction rate constant 2 at the plurality of temperatures based on the reaction rate equation from the remaining functional group ratio 2.

The fitting unit 40 calculates an activation energy Ea1 and a frequency factor A1 from the reaction rate constant 1 at the plurality of temperatures using an Arrhenius plot and calculates an activation energy Ea2 and a frequency factor A2 from the reaction rate constant 2 at the plurality of temperatures using an Arrhenius plot.

The polymerization catalyst selecting unit 50 determines whether the polymerization catalyst satisfies following Condition 1 based on the activation energies Ea1 and Ea2 or not.

Average value of $-Ea1/R$ and $-Ea2/R$ is $-7100$ or more and $-2900$ or less, preferably $-7050$ or more and $-4000$ or less. [Condition 1]

(R: gas constant (8.314 J/mol/K))

In a case where the polymerization catalyst is determined to satisfy Condition 1 in the polymerization catalyst selecting unit 50, the approximation equation setting unit 60 sets an approximation equation a from two amounts of the polymerization catalyst and the frequency factor A1 and the frequency factor A2 in the two catalyst amounts.

$\ln A = ax + b$                  Approximation equation a:

A: Frequency factor
a: Constant determined by the polymerization catalyst
b: Constant determined from two catalyst amounts and frequency factor A1 and frequency factor A2
x: Added amount of polymerization catalyst to be calculated (ppm)

The catalyst addition range setting unit 70 sets an addition range with a value obtained by multiplying a constant b in the approximation equation a by 1.003 or 1.2 set as the ln A, and each calculated polymerization catalyst added amount x set as a lower limit value and an upper limit value.

A detailed description will be given below.

In a case where the composition 1 including the polymerization-reactive compound and a predetermined amount of the polymerization catalyst is heated and maintained at a plurality of temperatures, the physical property acquiring unit 10 acquires the physical property value 1a derived from the functional groups of the polymerization-reactive compound before heating and the physical property value 1b derived from the remaining functional groups after maintaining a temperature for a predetermined time, from the storage unit 2, for example. Further, in a case where the composition 2, which is different from the composition 1 only in an amount of the polymerization catalyst, is heated and maintained at the plurality of temperatures, the physical property value 2a derived from the functional groups of the polymerization-reactive compound before heating and the physical property value 2b derived from the remaining functional groups after maintaining a temperature for a predetermined time are acquired (physical property acquiring step S10).

It is possible to carry out this step with at least one kind of polymerization catalyst and the physical property values described above are acquired for each catalyst.

The temperature at which the polymerization-reactive compound is heated varies depending on the temperature at which the polymerization-reactive compound is polymerized and, for example, it is possible to select one or more temperatures from a range of 5° C. or higher and 140° C. or lower. The temperature maintenance time depends on the temperature being maintained and is not particularly limited as long as the polymerization is not completed.

The storage unit 2 stores the physical property values 1a and 2a derived from a functional group before heating of the polymerization-reactive compound for each added amount and the physical property value 1b and 2b derived from the remaining functional group after maintaining a predetermined temperature for a predetermined time, in a composition formed of a combination of the polymerization-reactive compound described above and the polymerization catalyst described above. The physical property values 1b and 2b are stored in association with the use amount of the polymerization catalyst for various polymerization-reactive compounds and the heat maintenance temperature (the temperature after heating) and exist for at least one period of elapsed time for each of a plurality of heat maintenance temperatures. The physical property values 1a and 2a and the physical property values 1b and 2b are directly input to the storage unit 2 from an input unit not shown in the drawings.

The stored physical property values 1a and 2a and the physical property values 1b and 2b are the heat value, specific gravity, weight-average molecular weight, number-average molecular weight, spectral intensity in IR measurement, $^1$H-NMR spectral intensity, or $^{13}$C-NMR spectral intensity.

The physical property acquiring unit 10 is able to, for example, read out and acquire the physical property values 1a and 2a and the physical property values 1b and 2b stored in the storage unit 2. Specifically, the physical property acquiring unit 10 reads out and acquires the physical property value 1a and physical property value 1b for the composition 1 with a predetermined amount of catalyst and reads out and acquires the physical property value 2a and physical property value 2b for the composition 2 which is different from the composition 1 only in an amount of the catalyst.

It is also possible for the physical property values 1a and 2a and the physical property values 1b and 2b obtained by measuring devices such as a thermal analyzer, a specific gravity measuring device, a GPC measuring device, an IR measuring device, and an NMR device to be directly input to the physical property acquiring unit 10 from an input unit not shown in the drawings.

Specific examples of a thermal analyzer able to be used in the present embodiment include a differential scanning calorimeter, a calorimeter, a microcalorimeter, a differential calorimeter, a differential simultaneous thermo-gravimeteric analyzer, a thermogravimetric analyzer, a thermomechanical measuring device, a dynamic thermomechanical measuring device, and the like.

Next, the remaining functional group ratio calculating unit 20 acquires the physical property value 1a and physical property value 1b from the physical property acquiring unit 10, calculates the remaining functional group ratio 1 based on these physical property values, acquires the physical property value 2a and physical property value 2b from the physical property acquiring unit 10, and calculates the remaining functional group ratio 2 based on these physical property values (remaining functional group ratio calculating step S20).

A description will be given below of a case where the remaining functional group ratio calculating unit 20 calculates the remaining functional group ratio according to, for example, the amount of heat measured by thermal analysis.

It is possible to represent the remaining functional group ratio by Equation 1.

$$\text{Remaining functional group ratio} = Xt/X_0 \qquad \text{Equation 1:}$$

$X_0$ (J/g): Amount of heat measured by DSC thermal analysis of the prepared solution immediately after preparation (before polymerization)

$Xt$ (J/g): Amount of heat of the prepared solution after temperature maintenance at a specific temperature for t hours In the present embodiment, $X_0$ corresponds to the physical property values 1a and 2a and $Xt$ corresponds to the physical property values 1b and 2b. The remaining functional group ratio 1 is calculated from the physical property value 1a and physical property value 1b and the remaining functional group ratio 2 is calculated from the physical property value 2a and physical property value 2b.

For example, in a case of calculating the remaining functional group ratio based on the specific gravity, it is possible to represent the remaining functional group ratio by Equation 2.

$$\text{Remaining functional group ratio} = [1-[(\text{specific gravity measured after maintenance at a specific temperature for } t \text{ hours-specific gravity of prepared solution immediately after preparation (before heating)})/\Delta d]] \qquad \text{Equation 2:}$$

$\Delta d$ (increase amount in specific gravity for each 1% decrease in remaining functional groups) = [(specific gravity of cured resin-specific gravity of solution immediately after preparation)/100]

In the present embodiment, the specific gravity of the prepared solution immediately after the preparation (before heating) corresponds to the physical property value 1a or 2a, while the specific gravity measured after temperature maintenance at a specific temperature for t hours corresponds to the physical property value 1b or 2b. The remaining functional group ratio 1 is calculated from the physical property value 1a and physical property value 1b and the remaining functional group ratio 2 is calculated from the physical property value 2a and physical property value 2b.

In addition, with an IR measurement device, in a case where a (thio)urethane resin is used as a polymerization-reactive compound, it is possible to calculate the remaining functional group ratio by quantifying the change over time in the ratio of the spectral intensity of the NCO group and the CH group.

The reaction rate constant calculating unit 30 acquires the remaining functional group ratios 1 and 2 from the remaining functional group ratio calculating unit 20. Then, reaction kinetic analysis is performed based on the reaction rate equation to calculate the reaction rate constant 1 at the plurality of temperatures from the remaining functional group ratio 1, and to calculate the reaction rate constant 2 at the plurality of temperatures from the remaining functional group ratio 2 (reaction rate constant calculating step S30).

It is possible for the reaction rate constant calculating unit 30 to read out the reaction rate equation stored in advance in the storage unit 2.

Examples of reaction rate equations include an nth-order reaction rate equation (n is 0 or more), a Prout-Tompkins rate equation, a Bawn rate equation, a Leeson-Mattocks rate equation, and the like. The reaction rate constant calculating unit 30 is able to select an optimal equation based on the polymerizable composition and the order of the reaction.

Based on the reaction rate equation read out from the storage unit 2, the reaction rate constant calculating unit 30 calculates the reaction rate constant 1 based on the remaining functional group ratio 1 acquired from the remaining functional group ratio calculating unit 20, and calculates the reaction rate constant 2 based on the remaining functional group ratio 2 acquired from the remaining functional group ratio calculating unit 20.

A description will be given below of a case where the nth order reaction rate equation represented by Equation 3 is used.

$$kt = f(\text{remaining functional group ratio}) \qquad \text{Equation 3:}$$

k: nth order reaction rate constant (n is a real number which is 0 or more)

t: Temperature maintenance time f (remaining functional group ratio) is determined by the value of n with a function of the remaining functional group ratio.

In a graph in which the horizontal axis represents the temperature maintenance time t and the vertical axis represents f (1/remaining functional group ratio) into which the remaining functional group ratio of the target substance (polymerizable compound) in the sample is substituted, the reaction rate constant calculating unit 30 plots the remaining functional group ratio for each temperature maintenance time. The reaction rate constant calculating unit 30 acquires a regression line from the graph and acquires the slope of the regression line as the reaction rate constant k.

The reaction rate constant calculating unit 30 calculates the reaction rate constants 1 and 2, respectively, based on the remaining functional group ratios 1 and 2. It is also possible to store the calculated reaction rate constants 1 and 2 in the storage unit 2.

The fitting unit 40 obtains the reaction rate constants 1 and 2 from the reaction rate constant calculating unit 30 or the storage unit 2, calculates the activation energy Ea1 and the frequency factor A1 from the reaction rate constant 1 at the plurality of temperatures using an Arrhenius plot, and calculates the activation energy Ea2 and the frequency factor A2 from the reaction rate constant 2 at the plurality of temperatures using an Arrhenius plot (fitting step S40).

To determine the correlation between the reaction rate constant of the change in the polymerizable compound included in the sample and the temperature of the sample, for example, with the temperature of the sample for which the temperature is maintained being converted to the absolute temperature T and the reciprocal thereof on the horizontal axis and the natural logarithm of the reaction rate constant k at this temperature on the vertical axis, each point is plotted to obtain a regression line having a slope of (−Ea/R). This plot is called an Arrhenius plot.

Specifically, in a graph in which the vertical axis is Ln (k) and the horizontal axis is the reciprocal 1/T of the absolute temperature, the fitting unit 40 determines Ln (k) based on the obtained reaction rate constant and creates an Arrhenius plot by plotting in the graph. From the Arrhenius plot, a regression line and a regression line equation of Equation 4 are obtained.

$$y = ax + b \text{ (regression line)} \qquad \text{Equation 4:}$$

Then, the reciprocal of the desired absolute temperature T is substituted into the regression line determined as described above to calculate the reaction rate constant k at the absolute temperature T and, by substituting this reaction rate constant k into the reaction rate equation illustrated in Equation 3 determined as described above, the remaining functional group ratio in a case where the sample is placed at the absolute temperature T for t hours is calculated.

Specifically, the fitting unit 40 obtains Equation 5 by replacing y, a, x, and b in the regression line of Equation 4 with the following.

$$y = \mathrm{Ln}(k)$$

$$a = (-Ea/R)$$

$$x = (1/T)$$

$$b = \mathrm{Ln}(\text{frequency factor})$$

Ea: Activation energy ($\mathrm{J \cdot mol^{-1} \, K^{-1}}$)
R: Gas coefficient ($8.3145 \, \mathrm{J \cdot mol^{-1}}$)
T: Absolute temperature
A: Frequency factor $$\mathrm{Ln}(k) = (-Ea/R) \times (1/T) + \mathrm{Ln}(A) \qquad \text{Equation 5:}$$

Then, the fitting unit 40 calculates the activation energy Ea1 and the frequency factor A1 from the reaction rate constant 1 at the plurality of temperatures using Equation 5, and calculates the activation energy Ea2 and the frequency factor A2 from the reaction rate constant 2 at the plurality of temperatures using an Arrhenius plot. The fitting unit 40 stores the frequency factors A1 and A2 in the storage unit 2 in association with the amount of the polymerization catalyst.

The polymerization catalyst selecting unit 50 determines whether the polymerization catalyst satisfies following Condition 1 based on the activation energies Ea1 and Ea2 or not (polymerization catalyst selecting step S50).

Average value of $-Ea1/R$ and $-Ea2/R$ is $-7100$ or more and $-2900$ or less. [Condition 1]

(R: gas constant (8.314 J/mol/K))

Condition 1 is stored in the storage unit 2 and the polymerization catalyst selecting unit 50 accesses the storage unit 2 to acquire Condition 1. The polymerization catalyst selecting unit 50 also acquires the activation energies Ea1 and Ea2 from the storage unit 2. Then, the polymerization catalyst selecting unit 50 calculates the average value of $-Ea1/R$ and $-Ea2/R$ and determines whether or not the average value satisfies Condition 1.

In a case where there is a polymerization catalyst which does not satisfy Condition 1, the polymerization catalyst selecting unit 50 displays that fact on a monitor not shown in the drawings and stops subsequent steps in relation to the polymerization catalyst which does not satisfy Condition 1. It is possible for the user to confirm the display on the monitor, return to the physical property acquiring step, and select the polymerizable compound and the kind of polymerization catalyst again to acquire the physical properties.

Meanwhile, in a case where it is determined that Condition 1 is satisfied, the polymerization catalyst selecting unit 50 accesses the storage unit 2 and sends the frequency factor A1 and frequency factor A2 from the storage unit 2 to an approximation equation setting unit 60. Then, the approximation equation setting unit 60 sets the approximation equation a from the two amounts of the polymerization catalyst and the frequency factor A1 and frequency factor A2 at the two catalyst amounts (approximation equation setting step S60).

The approximation equation setting unit 60 acquires a constant a, which is determined from the polymerization catalyst, from the storage unit 2, and the constant b is calculated from the two catalyst amounts and the frequency factor A1 and the frequency factor A2.

$$\ln A = ax + b \qquad \text{Approximation equation a:}$$

A: Frequency factor
a: Constant determined by the polymerization catalyst
b: Constant determined from two catalyst amounts and frequency factor A1 and frequency factor A2
x: Added amount of polymerization catalyst to be calculated (ppm)

The catalyst addition range setting unit 70 sets an addition range with a value obtained by multiplying a constant b in the approximation equation a by 1.003 or 1.2 set as the ln A, and each calculated polymerization catalyst added amount x set as a lower limit value and an upper limit value (catalyst addition range setting step S70).

Lower limit value x: calculated from $1.003b = ax + b$.

Upper limit value x: calculated from $1.2b = ax + b$.

In the storage unit 2, data on the solubility and dispersibility of the polymerization catalyst with respect to the polymerizable compound, the necessary polymerization time, and the like are stored in association with the kind of the polymerizable compound and the kind of the polymerization catalyst. The catalyst addition range setting unit 70 accesses the storage unit 2 to acquire the data and selects one kind or a combination of n kinds (n is an integer of two or more) from the polymerization catalysts. Alternatively, it is also possible for the user to select one kind or any combination from the polymerization catalysts displayed on a monitor not shown in the drawings.

In a case where the polymerization catalyst is one kind, the catalyst addition range setting unit 70 calculates the lower limit value and upper limit value and sets the addition range as described above.

On the other hand, in a case where the polymerization catalyst is a combination of n kinds (n is an integer of two or more), the catalyst addition range setting unit 70 calculates the added amount $x_1$ to the added amount $x_n$ of the n kinds of polymerization catalysts so as to satisfy the following condition, and sets the addition ranges of each of the polymerization catalysts.

$$1.003 \leq \{[(a_1 \times x_1 + b_1)/b_1] + [(a_2 \times x_2 + b_2)/b_2] + \ldots + [(a_n \times x_n + b_n)/b_n]\} - (n-1) \leq 1.2 \qquad \text{[Condition]}$$

$a_1$ to $a_n$: Constants determined from n kinds of polymerization catalysts, respectively
$b_1$ to $b_n$: Constants determined from two catalyst amounts and frequency factor A1 and frequency factor A2, for respective n kinds of polymerization catalysts
$x_1$ to $x_n$: Added amounts (ppm) of respective n kinds of polymerization catalysts to be calculated The catalyst addition range setting unit 70 stores the addition range (lower limit value and upper limit value) of the polymerization catalyst in association with the polymerizable compound and the polymerization catalyst. In addition, the catalyst addition range setting unit 70 may be configured to be able to output the kind of the polymerizable compound and the use conditions of the polymerization catalyst (kind of polymerization catalyst and addition range thereof (lower limit value and upper limit value)) to a monitor or the like not shown in the drawings. Due to this, it is possible for the user to check the appropriate composition of the polymerizable composition (combination of polymerizable compound and polymerization catalyst, addition range of polymerization catalyst), and to determine the desired added amount of polymerization catalyst to prepare the polymerizable composition as described below.

According to the present embodiment, since the optimum addition range of the polymerization catalyst is set in the desired combination of the polymerizable compound and the polymerization catalyst, it is possible to obtain optical materials having an excellent appearance, in which the generation of optical distortion and striae is suppressed.

[Polymerization Condition Setting Method and Polymerization Condition Setting Apparatus]

In the following description, a storage unit 102, a polymerization catalyst amount determining unit 110, a reaction rate constant calculating unit 120, and a polymerization program calculating unit 130 of a polymerization condition setting apparatus 100 are not shown in a configuration of hardware units, but as blocks of functional units. The storage unit 102, the polymerization catalyst amount determining unit 110, the reaction rate constant calculating unit 120, and the polymerization program calculating unit 130 of the polymerization condition setting apparatus 100 are realized by any combination of hardware and software centered on the CPU of any computer, a memory, a program which implements the components of this figure loaded in the memory, storage media such as a hard disk which stores the program, and an interface for network connection. Then, there are various modifications of the implementation method and apparatuses.

Figure 2:
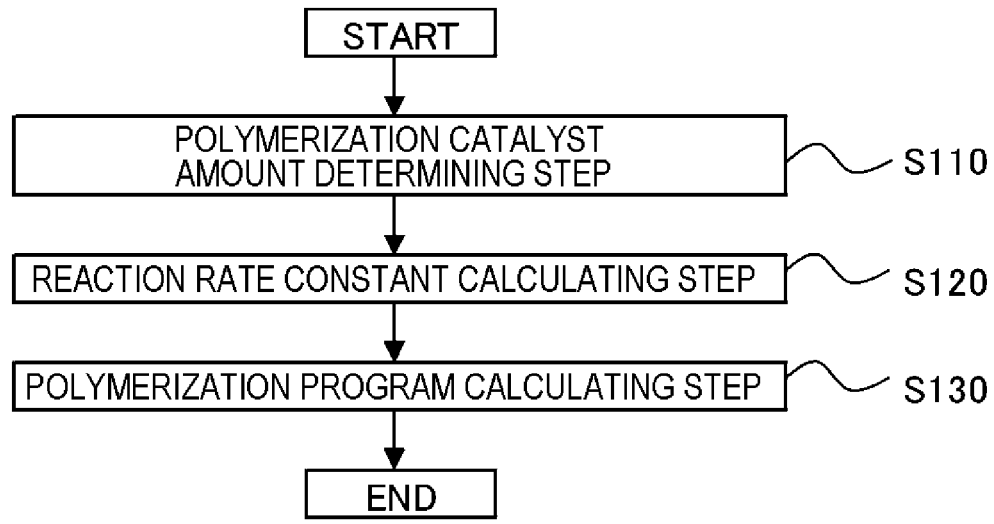
FIG. 2 is a flow chart of a polymerization condition setting method according to the present embodiment.

FIG. 2 is a flow chart of the polymerization condition setting method according to the present embodiment.

The polymerization condition setting method according to the present embodiment is a polymerization condition setting method based on the desired polymerization-reactive compound and polymerization catalyst use conditions obtained by the method for setting conditions for use of a polymerization catalyst described above.

As shown in FIG. 2, the polymerization condition setting method of the present embodiment includes a polymerization catalyst amount determining step S110, a reaction rate constant calculating step S120, and a polymerization program calculating step S130.

In the polymerization catalyst amount determining step S110, the kind of polymerization catalyst and the added amount y of a polymerization catalyst are determined from the kind of polymerization catalyst and the addition range of the polymerization catalyst with respect to the desired polymerizable compound set by the method for setting conditions for use of a polymerization catalyst described above.

In the reaction rate constant calculating step S120, reaction rate constants are calculated for each of the plurality of reaction temperatures T at the added amount y of the polymerization catalyst in Equation b derived from an approximation equation a and an Arrhenius equation.

$$k = \mathrm{Exp}[(-Ea/R) \times (1/T) + (ay+b)] \quad \text{Equation b:}$$

k: Reaction rate constant
−Ea/R: Value included in −7100 or more and −2900 or less, calculated in the polymerization catalyst selecting step S50

T: Desired reaction temperature (K)
a: Constant determined by the polymerization catalyst
b: Constant determined from two catalyst amounts and frequency factor A1 and frequency factor A2
y: Added amount of polymerization catalyst determined in polymerization catalyst amount determining step S110 (ppm)

In the polymerization program calculating step S130, the polymerization temperature program is back-calculated for each predetermined time in the polymerization time based on the reaction rate equation using the reaction rate constants described above, to satisfy the following conditions.

(Conditions)

An average polymerization rate from a 10% polymerization ratio point to an 80% polymerization ratio point is selected and determined in a range of 0.4%/hr or more and 15%/hr or less,
  a plurality of polymerization rates are calculated at every predetermined time in a time when a polymerization ratio is 10% or more and 80% or less,
  standard deviation, which is a positive square root of a dispersion of the plurality of polymerization rates and the average polymerization rate, is calculated, and
  the calculated standard deviation is 2.3%/hr or less.

It is possible to calculate the average polymerization rate from the 10% polymerization ratio point to the 80% polymerization ratio point by (80%−10%)/(t2−t1), where the 10% polymerization ratio point is t1 (hr) and the 80% polymerization ratio point is t2 (hr).

When calculating how the polymerization ratio increases (in other words, how the monomer concentration decreases) as time passes in the polymerization reaction, the calculations at each time are performed sequentially.

In the simulation of the present embodiment, the reaction temperature is calculated by calculating the reaction rate constant at the next time (t+Δt) based on the temperature and monomer concentration at time t. In the present embodiment, the temperature is the object to be calculated and it is possible to determine a temperature transition able to obtain the desired polymerization transition by calculation.

In the present embodiment, after the reaction rate (polymerization rate) in the time zone from time t to just before the next time (t+Δt) (the region where the value of time is t or more and less than t+Δt) is initially set to v, the reaction rate constant at the next time (t+Δt) is determined so that the reaction rate at the next time (t+Δt) also satisfies the condition of being equal to v.

For example, in the reaction between a polyisocyanate compound and an active hydrogen compound, when the concentration of the polyisocyanate compound is A and the concentration of the active hydrogen compound is B, a reaction rate (polymerization rate) v is expressed as $$v = k(T(t)) \times A(t) \times B(t) \quad \text{Equation a}$$

Here, k is a function of temperature. The temperature T and concentrations A and B are all functions of time t, and are denoted as T(t), A(t), and B(t). v is the reaction rate (average polymerization rate), which, in the present embodiment, is a value selected from a range of 0.4%/hr or more and 15%/hr or less.

The calculation is performed by changing equation a as follows.

$$k(T(t)) = v/(A(t) \times B(t)) \quad \text{Equation a'}$$

In the present embodiment, the temperature transition is determined by calculation so that the desired polymerization transition is obtained. Specifically, as described above, the reaction rate constant to be employed at time t+Δt is calculated based on the temperature and concentration of monomer at time t.

In Equation a', when time progresses by Δt, the concentrations A and B of the monomers decrease, respectively, thus, it is necessary to increase the value of k(T(t)) in order to keep v=constant, and how to change the value of k(T(t)) is determined by calculation.

A specific description will be given below of the calculation to determine k at time (t+Δt) based on the parameters at time t.

At time (t+Δt), equation a' is as follows.

$$k(T(t+\Delta t))=v/(A(t+\Delta t)\times B(t+\Delta t)) \quad \text{Equation b}$$

The polymerization rate in the time zone of time t or more and less than (t+Δt) is a selected average polymerization rate value and is expressed as follows.

$$A(t+\Delta t)=A(t)-v\times\Delta t \quad \text{Equation c1}$$

$$B(t+\Delta t)=B(t)-v\times\Delta t \quad \text{Equation c2}$$

When changing equation b based on equation c1 and equation c2, equation d is obtained.

$$k(T(t+\Delta t))=v/[(A(t)-v\times\Delta t)\times(B(t)-v\times\Delta t)] \quad \text{Equation d}$$

k(T(t)), A(t), and B(t) are known values previously determined by calculation in sequential calculation.

Next, the temperature (T(t+Δt)) is back-calculated from this k(T(t+Δt)).

The back-calculation is performed using the Arrhenius equation below, described as Equation 5.

$$\text{Ln}(k)=(-Ea/R)\times(1/T)+\text{Ln}(A) \quad \text{Equation 5:}$$

Ea: Activation energy (J·mol$^{-1}$K$^{-1}$)
R: Gas coefficient (8.3145 J·mol$^{-1}$)
T: Absolute temperature
A: Frequency factor It is possible to calculate the value of T uniquely from the calculated value of k(T(t+Δt)).

In the present embodiment, based on the various parameters (k(T(t)), A(t), and B(t)) at time t as described above, it is possible to calculate T(t+Δt) to be employed at time t+Δt.

Then, each polymerization temperature (plurality of T(t+Δt)) back-calculated at every predetermined time satisfies the condition that the standard deviation, which is the positive square root of the dispersion of the plurality of polymerization rates and the average polymerization rate calculated at every predetermined time, is 2.3%/hr or less.

In a polymerizable composition including a specific monomer and a specific amount y of a catalyst kind x, the viscosity of the polymerizable composition after several hours at a certain temperature is a physical property value inherent to the composition, thus, the viscosity is determined naturally. That is, specifying the polymerization ratio of a polymerizable composition is the same as specifying the viscosity of the polymerizable composition.

A description will be given below of the polymerization condition setting method and polymerization condition setting apparatus 100 according to the present embodiment.

Figure 4:
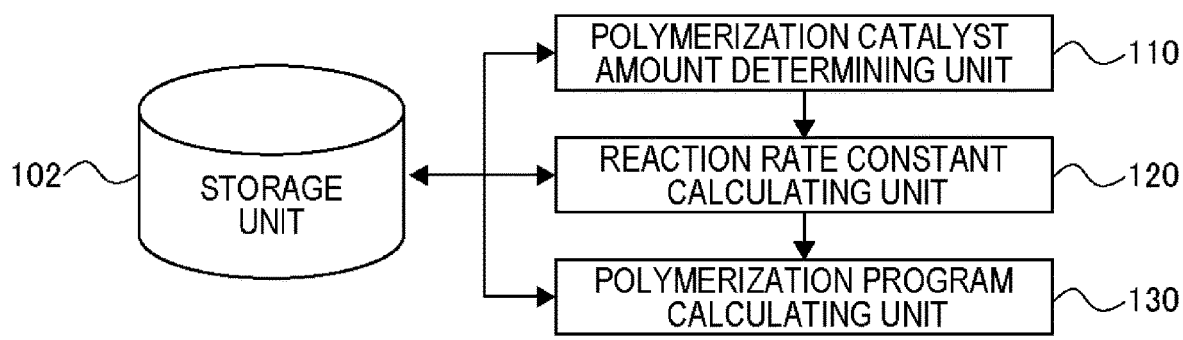
FIG. 4 is a block diagram showing a configuration of a polymerization condition setting apparatus according to the present embodiment.

FIG. 4 is a block diagram showing the polymerization condition setting apparatus 100 according to the present embodiment. The polymerization condition setting apparatus 100 according to the present embodiment is a polymerization condition setting apparatus based on the desired polymerization-reactive compound and polymerization catalyst use conditions obtained by the polymerization catalyst use condition setting apparatus described above.

The polymerization condition setting apparatus 100 is provided with a polymerization catalyst amount determining unit 110, a reaction rate constant calculating unit 120, and a polymerization program calculating unit 130.

The polymerization condition setting apparatus 100 is further provided with the storage unit 102. The storage unit is a computer-readable medium able to record measurement results, calculation results and programs. Examples thereof include semiconductor memories, IC cards, optical discs, magnetic disks, optical magnetic disks, magnetic tapes, digital video disks, and the like. It is possible for the program recorded in the storage unit to cause the computer to implement the method for setting conditions for use of a polymerization catalyst of the present embodiment.

It is also possible to configure the polymerization catalyst use condition setting apparatus 1 and the polymerization condition setting apparatus 100 as a single apparatus provided with a common storage unit.

The polymerization catalyst amount determining unit 110 determines the kind of polymerization catalyst and the added amount y of the polymerization catalyst from the kind and addition range of the polymerization catalyst with respect to the desired polymerizable compound set in the polymerization catalyst use condition setting apparatus 1.

The polymerization catalyst amount determining unit 110 is provided with an input unit not shown in the drawings, which makes it possible for the user to select the desired polymerizable compound and catalyst kind. The polymerization catalyst amount determining unit 110 is configured to be able to access the storage unit 2 and to acquire the desired polymerizable compound and the addition range of the catalyst kind from the storage unit 2.

In the storage unit 102, data on the solubility and dispersibility of the polymerization catalyst with respect to the polymerizable compound, the necessary polymerization time, and the like are stored in association with the kind of the polymerizable compound and the kind of the polymerization catalyst. The polymerization catalyst amount determining unit 110 accesses the storage unit 102 to acquire the data and determines the optimal added amount from the addition range of the polymerization catalyst kind, in the desired polymerizable compound and catalyst kind. It is also possible for the user to adjust the added amount.

When the added amount y of the polymerization catalyst is acquired from the polymerization catalyst amount determining unit 110, the reaction rate constant calculating unit 120 calculates the reaction rate constant for each of the plurality of reaction temperatures T at the added amount y of the polymerization catalyst in Equation b derived from the approximation equation a and the Arrhenius equation described above (reaction rate constant calculating step S120).

$$k=\text{Exp}[(-Ea/R)\times(1/T)+(ay+b)] \quad \text{Equation b:}$$

k: Reaction rate constant
−Ea/R: Value included in −7100 or more and −2900 or less, calculated in the polymerization catalyst selecting step
T: Desired reaction temperature (K)
a: Constant determined by the polymerization catalyst
b: Constant determined from two catalyst amounts and frequency factor A1 and frequency factor A2
y: Added amount of polymerization catalyst determined in the polymerization catalyst amount determining step (ppm)

The reaction rate constant calculating unit 120 accesses the storage unit 102 to determine one kind or a combination of n kinds (n is an integer of 2 or more) from the polymerization catalysts described above by referring to data on the solubility and dispersibility of the polymerization catalyst with respect to the polymerizable compound, as well as the necessary polymerization time and the like. Alternatively, it is also possible for the user to select one kind or any combination from the polymerization catalysts displayed on a monitor not shown in the drawings.

In a case where the polymerization catalyst is one kind, the reaction rate constant calculating unit 120 determines the optimum added amount from the addition range of the polymerization catalyst kind in the desired polymerizable compound and catalyst kind. It is also possible for the user to adjust the added amount. Then, the reaction rate constants are calculated for each reaction temperature T as described above.

On the other hand, in a case where the polymerization catalyst is a combination of n kinds (n is an integer of 2 or more), it is possible to determine the added amount $y_1$ to the added amount $y_n$ from the addition range of each polymerization catalyst kind. It is also possible for the user to adjust the added amount.

The reaction rate constant calculating unit 120 calculates the reaction rate constant $k_1$ to the reaction rate constant $k_n$ for each of the plurality of reaction temperatures T at the respective added amount $y_1$ to added amount $y_n$ of the n kinds of polymerization catalysts in Equation b derived from the approximate equation a and the Arrhenius equation.

$$k_i = \mathrm{Exp}[(-Ea/R) \times (1/T) + (a_i x_i + b_i)] \qquad \text{Equation b:}$$

$k_i$: Reaction rate constants $k_1$ to $k_n$ $-Ea/R$: Value included in $-7100$ or more and $-2900$ or less, calculated in the polymerization catalyst selecting step T: Desired reaction temperature (K)

$a_i$: Constant determined by respective n kinds of polymerization catalysts $b_i$: Constant determined from two catalyst amounts and frequency factor A1 and frequency factor A2 in each of n kinds of polymerization catalysts $x_i$: Added amounts $y_1$ to $y_n$ of each of n kinds of polymerization catalysts (ppm) determined by polymerization catalyst amount determining step Then, the reaction rate constant $k_\Sigma$ at each of the plurality of reaction temperatures T when using a combination of the n kinds of polymerization catalysts is calculated using Equation c.

$$k_\Sigma = \Sigma_{i=1}^{n} ki \qquad \text{Equation c:}$$

n: Integer of 2 or more

When the polymerization program calculating unit 130 acquires the reaction rate constants (k calculated by equation b and $k_\Sigma$ calculated by equation c) from the reaction rate constant calculating unit 120, the reaction rate constants are used to back-calculate the polymerization temperature program for each predetermined time in the polymerization time based on the reaction rate equation, to satisfy the following conditions.

The following conditions are stored in the storage unit 102, and when the polymerization program calculating unit 130 acquires the reaction rate constant from the reaction rate constant calculating unit 120, the polymerization program calculating unit 130 accesses the storage unit 102 to acquire the following conditions.

(Conditions)

An average polymerization rate from a 10% polymerization ratio point to an 80% polymerization ratio point is selected and determined in a range of 0.4%/hr or more and 15%/hr or less, a plurality of polymerization rates are calculated at every predetermined time in a time when a polymerization ratio is 10% or more and 80% or less, standard deviation, which is a positive square root of a dispersion of the plurality of polymerization rates and the average polymerization rate, is calculated, and the calculated standard deviation is 2.3%/hr or less.

The polymerization program calculating unit 130 sends the obtained polymerization program to the storage unit 102, and the storage unit 102 stores the polymerization program in association with the kind of polymerizable compound and the kind and added amount of polymerization catalyst.

The polymerization program calculating unit 130 may be configured to be able to output the polymerization program along with the kind of polymerizable compound and the kind and the added amount of the polymerization catalyst to a monitor or the like not shown in the drawings. Due to this, it is possible for the user to check the polymerization program in a case where the desired polymerizable compound and polymerization catalyst are used and to carry out the polymerization reaction according to these conditions.

The optical material manufacturing apparatus of the present embodiment is provided with the polymerization condition setting apparatus described above.

Specifically, the optical material manufacturing apparatus of the present embodiment is provided with:

the polymerization catalyst use condition setting apparatus 1 which sets a kind and an addition range of a polymerization catalyst with respect to a desired polymerizable compound, the polymerization condition setting apparatus 100 which calculates a polymerization program from the kind and addition range of the polymerization catalyst with respect to the desired polymerizable compound set in the setting apparatus 1, a heating unit which heats a composition including the desired polymerization-reactive compound and a predetermined amount of the polymerization catalyst, and a control unit which controls the heating unit to heat the composition including the polymerization-reactive compound and the polymerization catalyst based on the polymerization program obtained by the polymerization condition setting apparatus 100.

The heating unit is a device which is able to heat a mold filled with a composition and examples of heating furnaces include an electric furnace, a hot-air circulation furnace, an infrared oven, a microwave oven, and the like.

The control unit may be installed integrally with or separately from the heating furnace and may be provided with a means for measuring a heat value (for example, measurement of the temperature distribution in the oven, the outer surface temperature of the mold, the inner surface temperature of the mold, and the temperature in the polymerizing step until the composition is cured) and a monitor. Furthermore, the control unit is configured so as to be able to access the storage unit 102 of the polymerization condition setting apparatus 100 and to monitor the temperature of the heating unit.

After the start of the polymerization, the control unit monitors the temperature of the polymerization composition, compares the temperature with the polymerization temperature conditions for each polymerization time obtained from a storage unit 100, and controls the heating unit based on the polymerization temperature conditions.

The optical material manufacturing apparatus of the present embodiment is able to suitably execute the polymerization condition setting method of the present embodiment.

According to the optical material manufacturing apparatus of the present embodiment, it is possible to implement the method for manufacturing an optical material of the present embodiment including a step of preparing a polymerizable composition by mixing the polymerizable compound and the polymerization catalyst kind in added amounts set by the polymerization condition setting method of the present embodiment, a step of introducing the polymerizable composition into a mold, and a step of polymerizing and curing the polymerizable composition so as to satisfy polymerization temperature conditions for each polymerization time calculated by the polymerization condition setting method of the present embodiment.

Embodiments of the present invention were described above with reference to the drawings; however, the above are merely examples of the present invention and it is also possible to adopt various other configurations.

EXAMPLES

A more detailed description will be given of the present invention using Examples, but the present invention is not limited thereto.

Example 1

[Selection of Catalyst Usability]

In a flask with a stirrer, 23.9 parts by weight of pentaerythritol tetrakis (3-mercaptopropionate) and 0.100 parts by weight of an internal release agent for MR were added to 25.5 parts by weight of 4-mercaptomethyl-1,8-dimercapto-3,6-dithiaoctane, stirred, and 0.007 parts by weight of 2,4,6-collidine, which is a catalyst (set at 70 ppm/catalyst amount 1) were added to the solution and stirred. After adjusting the temperature of the solution to 15° C. in a constant temperature bath, 50.6 parts by weight of a mixture of 2,5-bis(isocyanatomethyl)bicyclo-[2.2.1]-heptane and 2,6-bis(isocyanatomethyl)bicyclo-[2.2.1]-heptane, and 1.50 parts by weight of a UV absorber (VIOSORB 583) were introduced, stirred and mixed, and quickly mixed and stirred at 15° C. Approximately 0.5 g of the stirred solution was placed as two samples (for two test temperatures) in sample bottles and rapidly depressurized and degassed by a vacuum pump.

Thereafter, the reduced pressure was returned to atmospheric pressure. The heat value of the sample immediately after the preparation was measured using a differential scanning calorimeter as a reaction time of zero hours. The sample bottles of the two samples were subjected to nitrogen substitution and analysis was performed by a differential scanning calorimeter two times at 20° C. after time elapsed (after 0 hours, and after 22 hours) and two times at 60° C. after time elapsed (after 0 hours and after 1 hour) to obtain heat values.

Heat value after 0 hours at 20° C.: 533.7 (J/g)
Heat value after 22 hours at 20° C.: 487.3 (J/g)
Heat value after 0 hours at 60° C.: 533.7 (J/g)
Heat value after 1 hour at 60° C.: 518.4 (J/g)

The heat values described above were directly input and stored in the storage unit 2 and the kind and addition range of the polymerization catalyst were calculated by the setting apparatus 1 of the present invention.

The physical property acquiring unit 10 acquires and sends the heat value described above from the storage unit 2 to the remaining functional group ratio calculating unit 20. The remaining functional group ratio calculating unit 20 calculated the remaining functional group ratio from these heat values. At 20° C., the remaining functional group ratio at 0 hour immediately after mixing and stirring was 1.0000 and the remaining functional group ratio after 22 hours was 0.9131 and, at 60° C., the remaining functional group ratio at 0 hour immediately after mixing and stirring was 1.0000 and the remaining functional group ratio after 1 hour was 0.9713.

The reaction rate constant calculating unit 30 used a second-order reaction rate equation and the reaction rate constant, which is the slope of the regression line, obtained results of 0.0043 at 20° C. and 0.0259 at 60° C.

In the same operation as the operation above, acquisition was carried out by changing the amount of 2,4,6-collidine catalyst. The above was carried out in the same manner except that the amount of 2,4,6-collidine was changed to 0.063 parts by weight (630 ppm/catalyst amount 2), and carried out until the prepared solution was degassed and returned to atmospheric pressure. The heat value of the sample immediately after the preparation was measured using a differential scanning calorimeter as a reaction time of zero hours. The sample bottles of the two samples were subjected to nitrogen substitution, analysis was performed by a differential scanning calorimeter two times at each elapsed time (after 0 hours and 3 hours) at 20° C. and two times at each elapsed time (after 0 hours and 1 hour) at 60° C. to obtain heat values.

Heat value after 0 hours at 20° C.: 533.7 (J/g)
Heat value after 3 hours at 20° C.: 495.2 (J/g)
Heat value after 0 hours at 60° C.: 533.7 (J/g)
Heat value after 1 hour at 60° C.: 464.7 (J/g)

The heat values described above were directly input into the storage unit 2 and stored.

The remaining functional group ratio calculating unit 20 acquired the heat values from the storage unit 2 and calculated the remaining functional group ratio from these heat values. Results were obtained in which, at 20° C., the remaining functional group ratio at 0 hour immediately after mixing and stirring was 1.0000 and the remaining functional group ratio after 3 hours was 0.9278 and, at 60° C., the remaining functional group ratio at 0 hour immediately after mixing and stirring was 1.0000 and the remaining functional group ratio after 1 hour was 0.8707.

The reaction rate constant calculating unit 30 used a second-order reaction rate equation and the reaction rate constant, which is the slope of the regression line, obtained results of 0.0259 at 20° C. and 0.1485 at 60° C.

The fitting unit 40 created Arrhenius plots using the reaction rate constants at 20° C. and 60° C. for 70 ppm (catalyst amount 1) and 630 ppm (catalyst amount 2) obtained from the reaction rate constant calculating unit 30. $1/T(K^{-1})$ was plotted on the horizontal axis and Ln (the reaction rate constant) at 20° C. and 60° C. for each catalyst amount was plotted on the vertical axis.

Using Arrhenius plots, the fitting unit 40 calculated the activation energy Ea and the frequency factor at 70 ppm (catalyst amount 1), as well as calculating the activation energy Ea and the frequency factor at 630 ppm (catalyst amount 2). The calculation results were stored in the storage unit.

$$\text{Ln(reaction rate constant)} = (\text{slope}) \times (1/T) + \text{Ln(frequency factor)} \quad \text{(Equation I)}$$

Slope: $-Ea/R$

The polymerization catalyst selecting unit 50 obtained the activation energy Ea at 70 ppm (catalyst amount 1) and 630 ppm (catalyst amount 2) from the fitting unit 40, and determined the slope (average value) at the 70 ppm and 630 ppm catalyst amounts from the regression line equation. As a result, the slope ($-Ea/R$) was $-4482.7$.

The polymerization catalyst selecting unit 50 accessed the storage unit 2 and acquired the condition for determining whether or not the catalyst kind was acceptable, which was "slope $-7100$ or more and $-2900$ or less", the calculated slope was in the above range, the 2,4,6-collidine catalyst was determined as useable in a monomer configuration of a thiol compound and an isocyanate compound. The results were stored in the storage unit 2. The results are shown in Table-1 as No. 3.

Table-1 shows the results acquired in the same manner as described above by changing the catalyst kind and monomer kind.

Example 2

[Calculating Appropriate Range of Catalyst Amount]

The range of the use amount was back-calculated for the catalysts determined to be usable in the catalyst kind selection simulation of Example 1.

The method of back-calculating the amount of catalyst used will be illustrated using the results implemented in Example 1.

In a case where the polymerization catalyst selecting unit 50 determines that it is possible to use a 2,4,6-collidine catalyst in the monomer configuration of thiol compounds (compound a1, compound a2) and isocyanate compounds (compound b1), that fact is sent to the approximation equation setting unit 60.

The storage unit 2 stores Ln (frequency factor) 10.611 for 70 ppm (catalyst amount 1) and Ln (frequency factor) 10.885 for 630 ppm (catalyst amount 2) calculated by the fitting unit 40 using Equation I and the approximation equation setting unit 60 accesses the storage unit 2 and acquires Ln (frequency factor) for 70 ppm (catalyst amount 1), and Ln (frequency factor) for 630 ppm (catalyst amount 2).

From these results, the catalyst amount was plotted on the horizontal axis and Ln (frequency factor) on the vertical

TABLE 1

Polymerization catalyst kind selection simulation

| | Thiol compound (parts by weight) | | | Isocyanate compound (parts by weight) | | | | Additive (parts by weight) | | | Slope | Simulation |
|---|---|---|---|---|---|---|---|---|---|---|---|---|
| No. | a1 | a2 | a3 | b1 | b2 | b3 | b4 | c1 | d1 | Catalyst kind | ($-Ea/R$) | results |
| 1 | 25.5 | 23.9 | — | 50.6 | — | — | — | 0.100 | 1.50 | Pyridine | $-1814$ | Unusable |
| 2 | 25.5 | 23.9 | — | 50.6 | — | — | — | 0.100 | 1.50 | Tetra-n-butyl phosphonium bromide | $-74$ | Unusable |
| 3 | 25.5 | 23.9 | — | 50.6 | — | — | — | 0.100 | 1.50 | 2,4,6-collidine | $-4483$ | Usable |
| 4 | 25.5 | 23.9 | — | 50.6 | — | — | — | 0.100 | 1.50 | N,N-dimethylbenzylamine | $-3162$ | Usable |
| 5 | 25.5 | 23.9 | — | 50.6 | — | — | — | 0.100 | 1.50 | Triethylamine | $-1518$ | Unusable |
| 6 | 25.5 | 23.9 | — | 50.6 | — | — | — | 0.100 | 1.50 | 3,5-lutidine | $-3397$ | Usable |
| 7 | 25.5 | 23.9 | — | 50.6 | — | — | — | 0.100 | 1.50 | Dimethyltin dichloride | $-7014$ | Usable |
| 8 | — | — | 50.7 | — | 49.3 | — | — | 0.100 | 1.50 | 2,4,6-collidine | $-4193$ | Usable |
| 9 | — | 14.7 | 33.1 | — | — | 24.1 | 28.2 | 0.100 | 1.50 | 3,5-lutidine | $-4457$ | Usable |

The compounds listed in Table-1 are as follows. The same applies to Table-2 and Table-3 described below.
- a1: 4-mercaptomethyl-1,8-dimercapto-3,6-dithiaoctane
- a2: Pentaerythritol tetrakis(3-mercaptopropionate)
- a3: Mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane
- b1: Mixture of 2,5-bis(isocyanatomethyl)bicyclo-[2.2.1]-heptane and 2,6-bis(isocyanatomethyl)bicyclo-[2.2.1]-heptane
- b2: m-xylylene diisocyanate
- b3: 1,5-pentane diisocyanate
- b4: 2,4,6-tris(5-isocyanatopentyl)cyclohexane-1,3,5-trione
- c1: Internal release agent for MR
- c2: Internal release agent ZelecUN
- d1: UV absorber VIOSORB 583 axis, and the regression line expressed by approximation equation II was obtained. a was a constant determined uniquely from 2,4,6-collidine, and b was a constant determined from the two catalyst amounts and the two frequency factors.

$$y = ax + b \quad \text{(Equation II)}$$

y: Ln (frequency factor)
a: Constant 0.0005
x: Added amount of 2,4,6-collidine (ppm)
b: Constant 10.577

The approximation equation setting unit 60 obtained Equation III as a result.

$$\text{Ln(frequency factor)} = [0.0005 \times (\text{added amount of 2,4,6-collidine})] + 10.577. \quad \text{(Equation III)}$$

When the catalyst addition range setting unit 70 obtained Equation III from the approximation equation setting unit

60, in order to determine the appropriate range of the catalyst added amount, it determined that, the values obtained by multiplying 10.577, which is term b of Equation III, by 1.003 and 1.200 were 10.609 and 12.692. To obtain the range of the determined Ln (frequency factor), Equation IV and Equation V were used to determine the added amount range of 2,4,6-collidine. The results are shown below.

$10.609 = [0.0005 \times 2,4,6\text{-collidine added amount}] + 10.577$ 2,4,6-collidine added amount (lower limit value) =
$(10.609 - 10.577)/0.0005 = 64$ ppm   (Equation IV to determine lower limit value of catalyst added amount)

$12.692 = [0.0005 \times 2,4,6\text{-collidine added amount}] + 10.577$ 2,4,6-collidine added amount (upper limit value) =
$(12.692 - 10.577)/0.0005 = 4231$ ppm   (Equation V to determine upper limit value of catalyst added amount)

From the above results, for the appropriate catalyst added amount, the 2,4,6-collidine catalyst added amount was 64 ppm or more, and the upper limit value was 4231 ppm or less. The results are shown in Table-1 as No. 3. The results were stored in the storage unit 2 in association with the catalyst kind, monomer kind, and the like, and displayed on a monitor not shown in the drawings.

For the catalysts determined to be usable in Example 1, as shown in Table-1, the range of catalyst use amount was back-calculated in the same manner as described above. The results are shown in Table-2. In this manner, it was possible to select the catalyst kind necessary to create the lens and back-calculate the catalyst added amount range.

Example 3

When the kind and combination of polymerizable compounds and the like were input, the polymerization catalyst amount determining unit 110 determined the desired polymerization catalyst and the added amount thereof from the results obtained in Example 2. In the present Example, compound a1 and compound a2 were input as thiols and compound b1 as isocyanate, and the polymerization catalyst amount determining unit 110 determined 2,4,6-collidine as the polymerization catalyst based on predetermined data (solubility and dispersibility of the polymerization catalyst with respect to the polymerizable compound, necessary polymerization time, and the like) acquired from the storage unit 102, and, as the added amount thereof, 300 ppm was determined from the added amount range of 64 ppm to 4231 ppm.

Equation VI, obtained by substituting Equation II into Equation I, is stored in the storage unit 102 to set the temperature program conditions for the polymerization reaction.

$\text{Ln(reaction rate constant)} = [(-E_a/R) \times (1/T)] + [(a \times \text{catalyst added amount (300 ppm)}) + b]$   (Equation VI)

a: Constant 0.0005 b: Constant 10.577

T: Reaction temperature $E_a$: Activation energy

R: Gas constant (8.314 J/mol/K)

The reaction rate constant calculating unit 120 obtained Equation VII (Equation b) by changing Equation VI obtained from the storage unit 102, and determined the reaction rate constant from the polymerization catalyst kind

TABLE 2

Polymerization catalyst amount setting simulation

| No. | Thiol compound (parts by weight) | | | Isocyanate compound (parts by weight) | | | | Additive (parts by weight) | | Catalyst kind |
|---|---|---|---|---|---|---|---|---|---|---|
| | a1 | a2 | a3 | b1 | b2 | b3 | b4 | c1 | d1 | |
| 3 | 25.5 | 23.9 | — | 50.6 | — | — | — | 0.100 | 1.50 | 2,4,6-collidine |
| 4 | 25.5 | 23.9 | — | 50.6 | — | — | — | 0.100 | 1.50 | N,N-dimethylbenzylamine |
| 6 | 25.5 | 23.9 | — | 50.6 | — | — | — | 0.100 | 1.50 | 3,5-lutidine |
| 7 | 25.5 | 23.9 | — | 50.6 | — | — | — | 0.100 | 1.50 | Dimethyltin dichloride |
| 8 | — | — | 50.7 | — | 49.3 | — | — | 0.100 | 1.50 | 2,4,6-collidine |
| 9 | — | 14.7 | 33.1 | — | — | 24.1 | 28.2 | 0.100 | 1.50 | 3,5-lutidine |

| No. | Ln (frequency factor) = ax + b | Term b × constant | | Catalyst added amount range (ppm) | |
|---|---|---|---|---|---|
| | | Term b × 1.003 | Term b × 1.200 | Lower limit value | Upper limit value |
| 3 | 0.0005x(catalyst added amount ppm) + 10.577 | 10.609 | 12.692 | 63 | 4231 |
| 4 | 0.0122x(catalyst added amount ppm) + 5.032 | 5.047 | 6.038 | 1 | 82 |
| 6 | 0.0045x(catalyst added amount ppm) + 6.113 | 6.131 | 7.336 | 4 | 272 |
| 7 | 0.0028x(catalyst added amount ppm) + 18.146 | 18.200 | 21.775 | 19 | 1296 |
| 8 | 0.0194x(catalyst added amount ppm) + 8.485 | 8.510 | 10.182 | 1 | 87 |
| 9 | 0.0031x(catalyst added amount ppm) + 12.102 | 12.138 | 14.522 | 12 | 781 | and the added amount thereof obtained from the polymerization catalyst amount determining unit 110.

Reaction rate constant=EXP[[(−Ea/R)×(1/T)]+[(a× catalyst added amount (300 ppm))+b]]   (Equation VII)

At the selected catalyst kind "2,4,6-collidine" and the appropriate catalyst added amount "300 ppm" thereof, the reaction rate constant was calculated for every 0.1° C. finely divided temperature using Equation VII.

Figure 5:
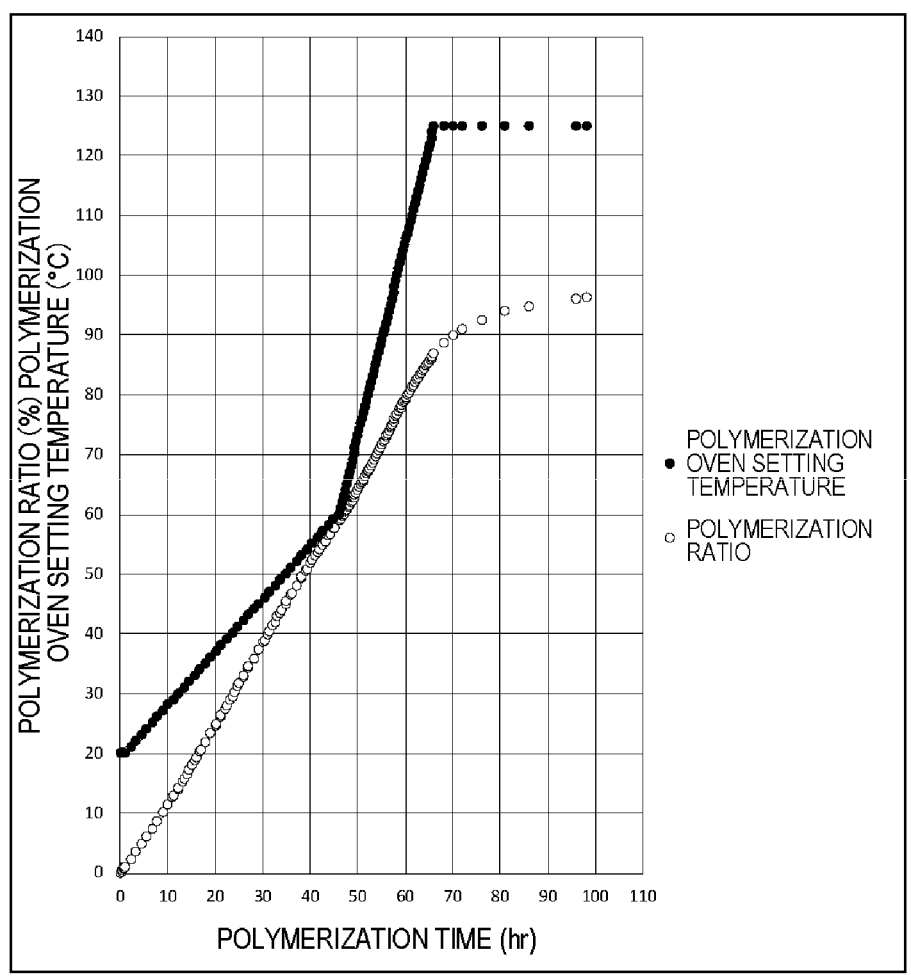
FIG. 5 is a chart plotting a polymerization oven setting temperature for each polymerization time (setting temperature program) and a chart plotting a polymerization ratio for each polymerization time, in Example 3.
Figure 6:
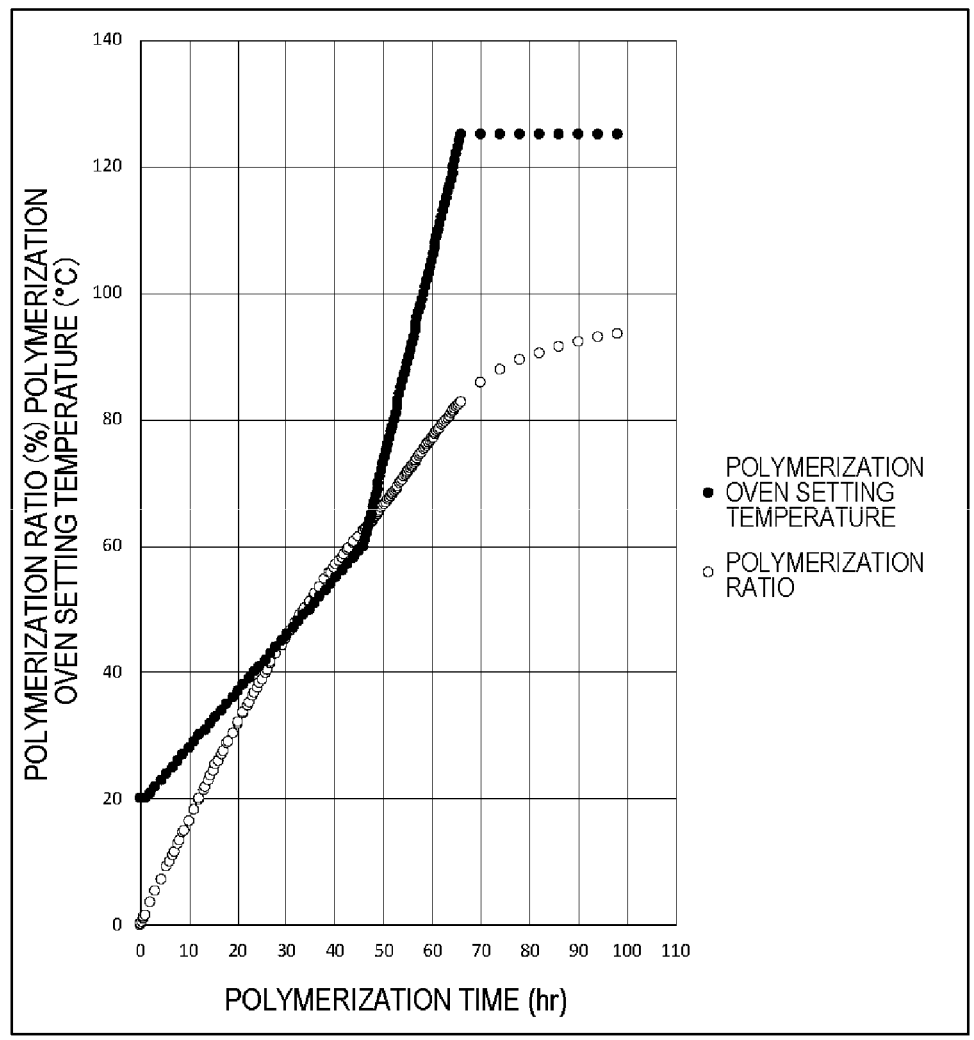
FIG. 6 is a chart plotting a polymerization oven setting temperature for each polymerization time (setting temperature program) and a chart plotting a polymerization ratio for each polymerization time, in Example 4.
Figure 7:
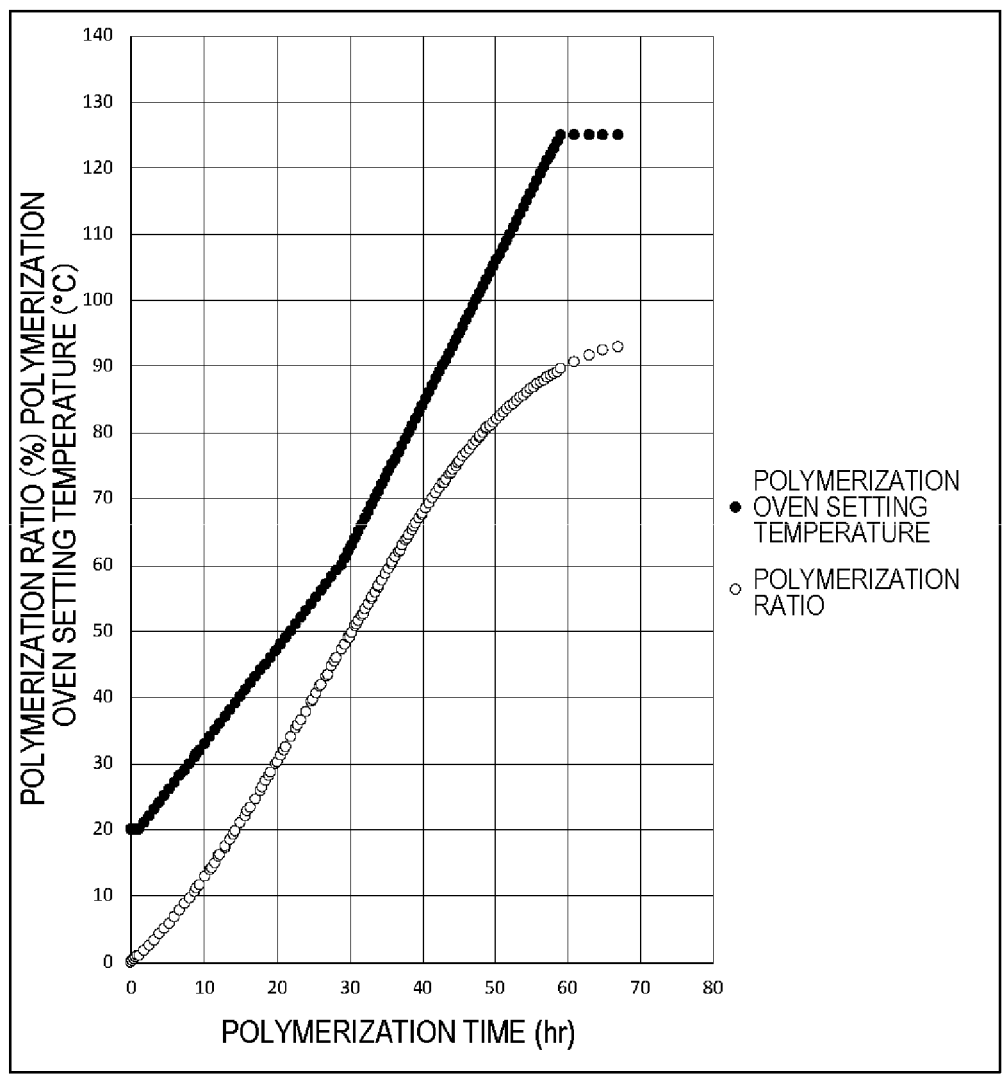
FIG. 7 is a chart plotting a polymerization oven setting temperature for each polymerization time (setting temperature program) and a chart plotting a polymerization ratio for each polymerization time, in Example 5.
Figure 8:
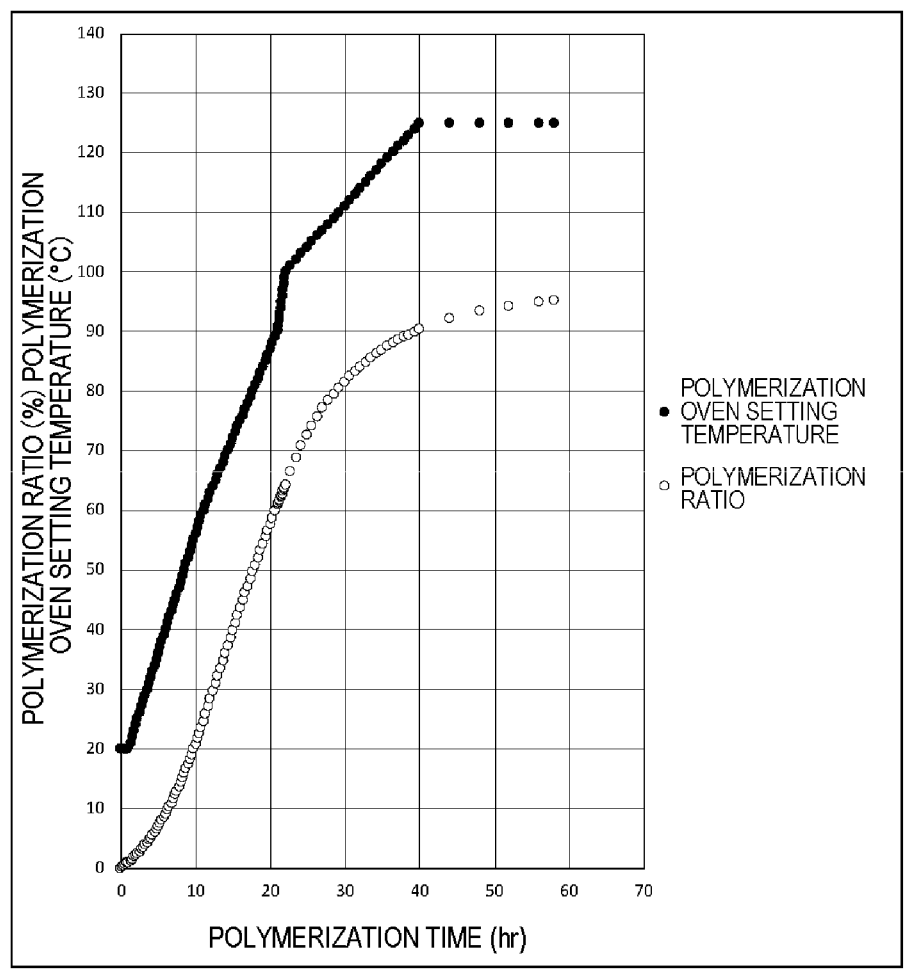
FIG. 8 is a chart plotting a polymerization oven setting temperature for each polymerization time (setting temperature program) and a chart plotting a polymerization ratio for each polymerization time, in Example 6.
Figure 9:
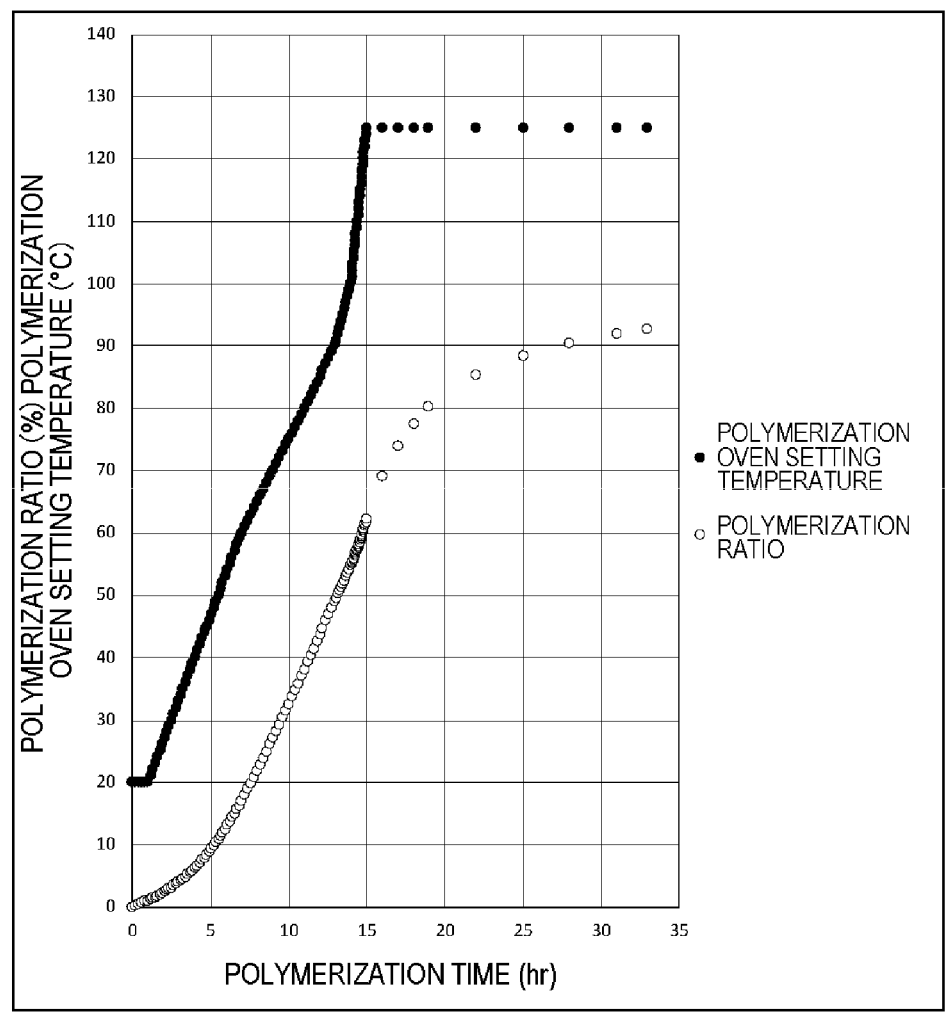
FIG. 9 is a chart plotting a polymerization oven setting temperature for each polymerization time (setting temperature program) and a chart plotting a polymerization ratio for each polymerization time, in Example 7.
Figure 10:
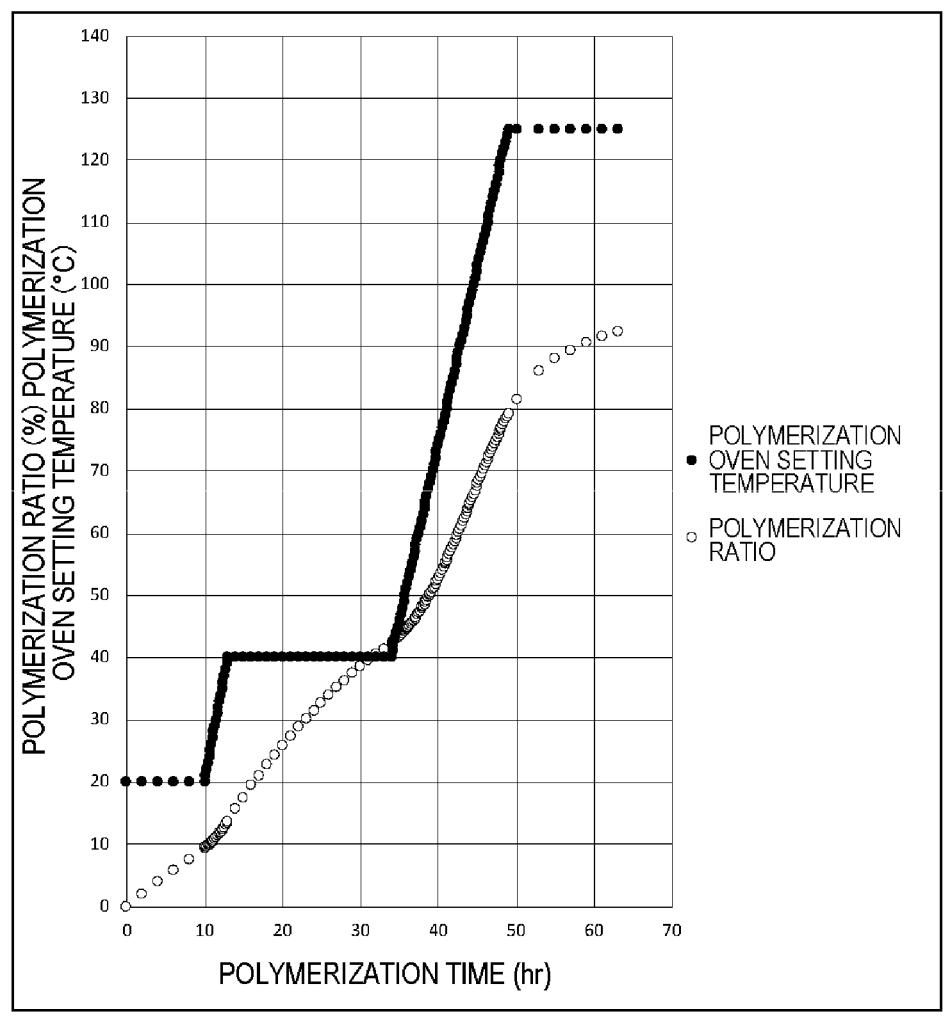
FIG. 10 is a chart plotting a polymerization oven setting temperature for each polymerization time (setting temperature program) and a chart plotting a polymerization ratio for each polymerization time, in Example 8.
Figure 11:
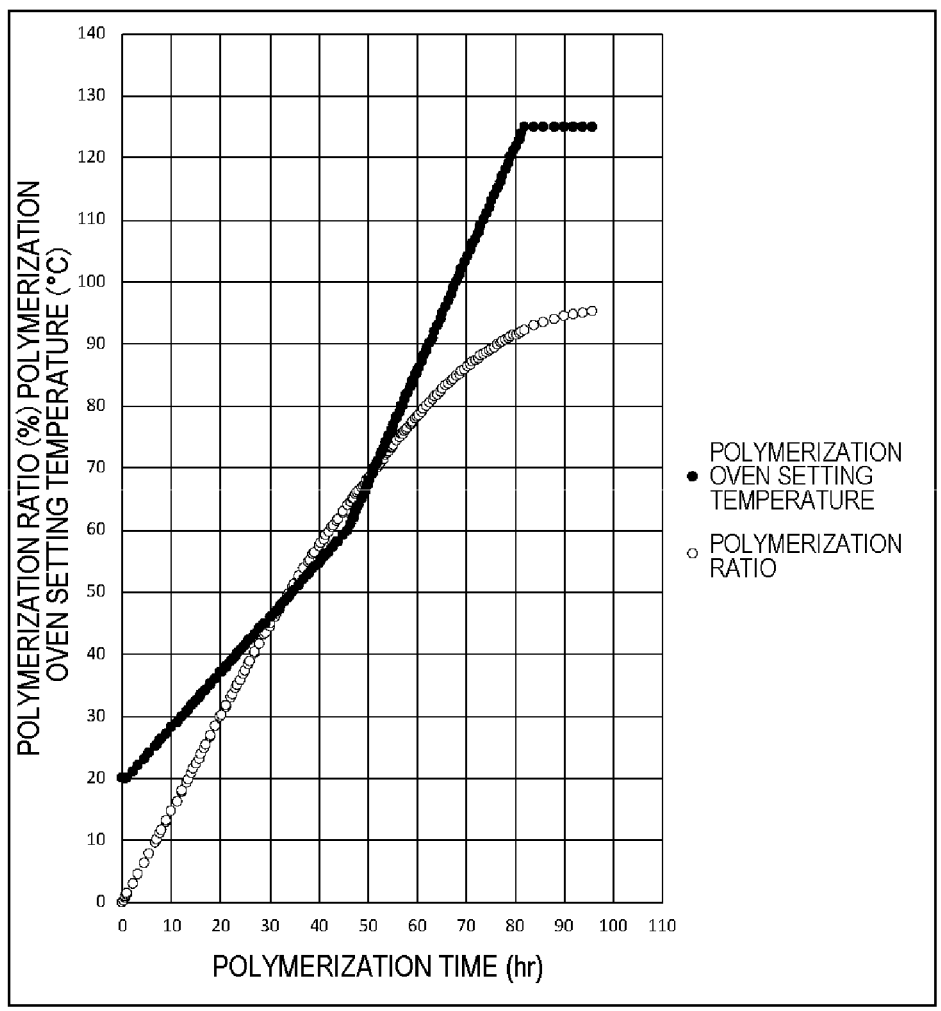
FIG. 11 is a chart plotting a polymerization oven setting temperature for each polymerization time (setting temperature program) and a chart plotting a polymerization ratio for each polymerization time, in Example 9.
Figure 12:
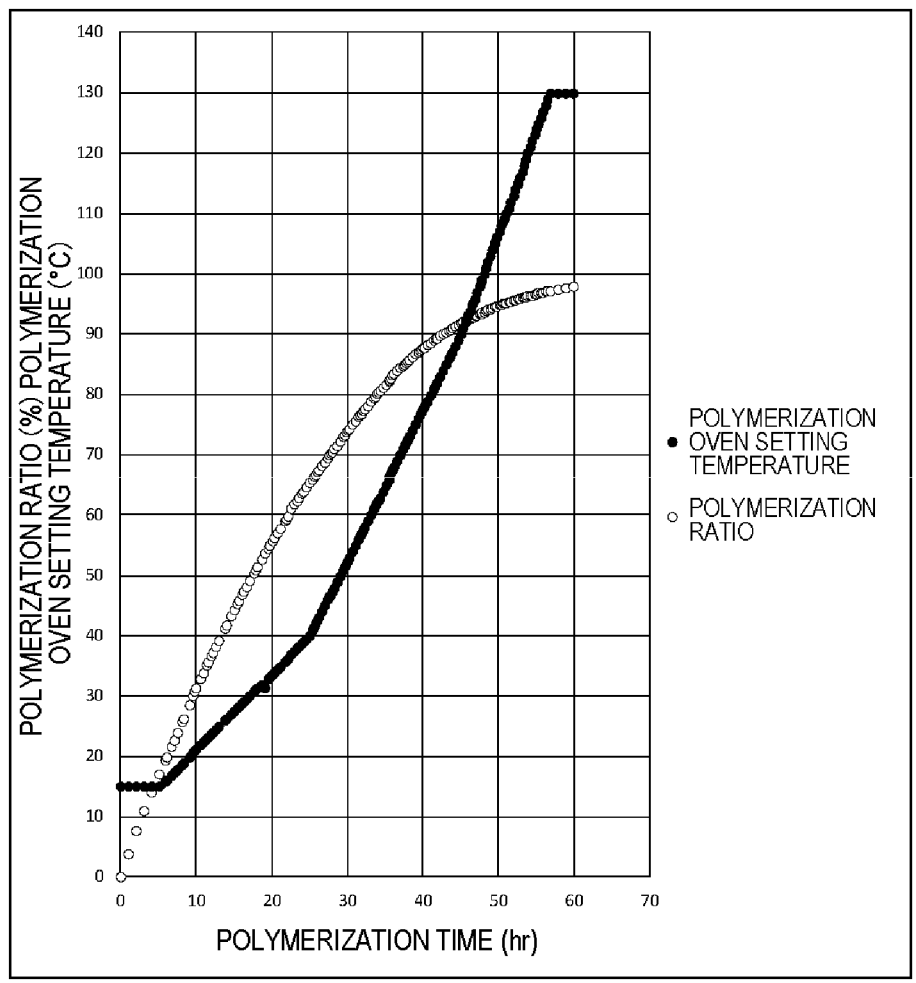
FIG. 12 is a chart plotting a polymerization oven setting temperature for each polymerization time (setting temperature program) and a chart plotting a polymerization ratio for each polymerization time, in Example 10.
Figure 13:
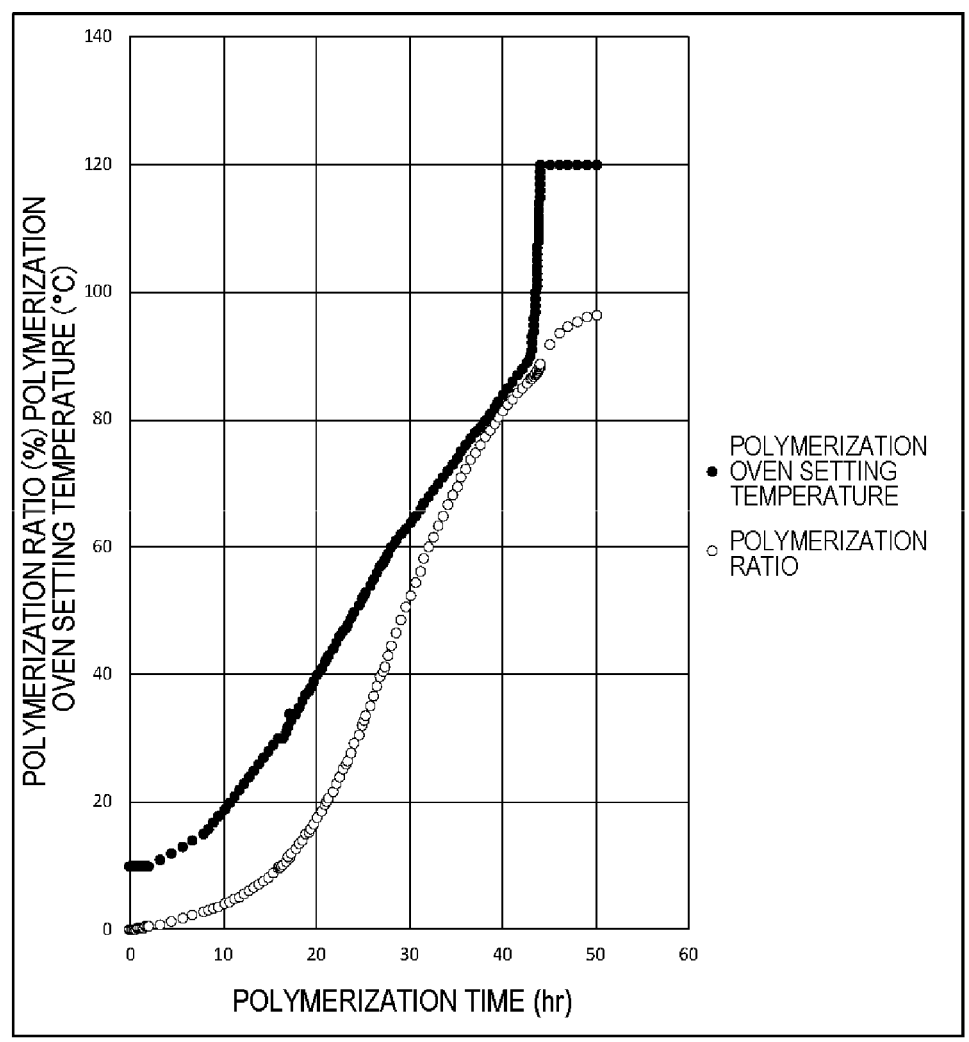
FIG. 13 is a chart plotting a polymerization oven setting temperature for each polymerization time (setting temperature program) and a chart plotting a polymerization ratio for each polymerization time, in Example 11.
Figure 14:
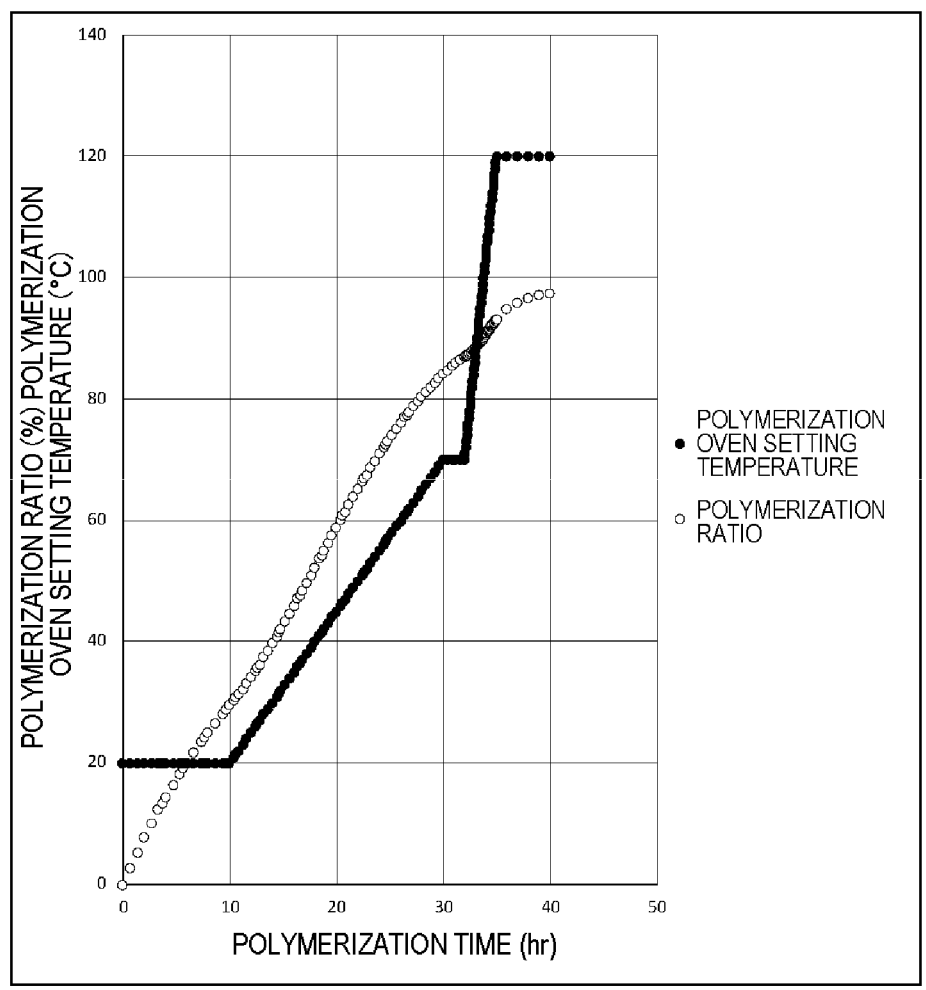
FIG. 14 is a chart plotting a polymerization oven setting temperature for each polymerization time (setting temperature program) and a chart plotting a polymerization ratio for each polymerization time, in Example 12.
Figure 15:
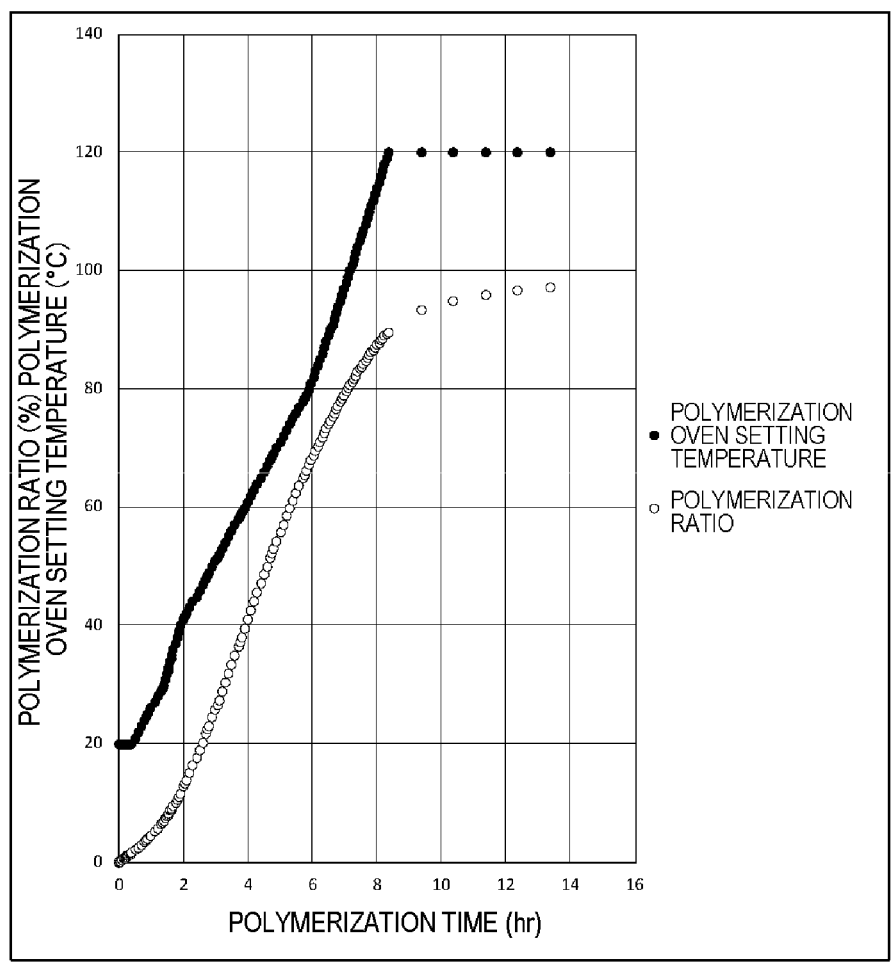
FIG. 15 is a chart plotting a polymerization oven setting temperature for each polymerization time (setting temperature program) and a chart plotting a polymerization ratio for each polymerization time, in Example 13.

The polymerization program calculating unit 130 used the obtained reaction rate constants to back-calculate the polymerization ratio and polymerization temperature for each polymerization time by the Arrhenius equation based on the reaction rate constants for every 0.1° C. temperature, to satisfy the following conditions. FIG. 5 shows a chart which plots the polymerization temperature conditions for every polymerization time, the polymerization time, and the polymerization ratio, which are displayed on a monitor not shown in the drawings.

(Conditions)

The average polymerization rate from the 10% polymerization ratio point to the 80% polymerization ratio point is 1.36%/hr.

The plurality of polymerization rates are calculated at every predetermined time (every 60 minutes) in the time when the polymerization ratio is 10% or more and 80% or less, and, the standard deviation, which is the positive square root of the dispersion of the plurality of polymerization rates and the average polymerization rate, is 0.12%/hr.

In an apparatus capable of stirring, 239 parts by weight of pentaerythritol tetrakis(3-mercaptopropionate) and 1.00 part by weight of internal release agent for MR were added to 255 parts by weight of 4-mercaptomethyl-1,8-dimercapto-3,6-dithiaoctane, stirring was carried out, 0.30 parts by weight of 2,4,6-collidine, which is a catalyst, were added to the solution and stirred. After adjusting the temperature of the solution to 15° C. in a constant temperature bath, 506 parts by weight of a mixture of 2,5-bis(isocyanatomethyl)bicyclo-[2.2.1]-heptane and 2,6-bis(isocyanatomethyl)bicyclo-[2.2.1]-heptane, and 15.0 parts by weight of a UV absorber (VIOSORB 583) were introduced and mixed and stirred at 15° C. The obtained prepared solution was sufficiently decompressed and degassed, and then returned to atmospheric pressure.

One thin mold (as Shape 1) had a front surface of 2 curves/back surface of 2 curves and a center thickness of 2 mm, and the other (as Shape 2) had a front surface of −400/back surface of FA450 and a center thickness of 1.2 mm. One thick mold (as Shape 3) had a front surface of 6 curves/back surface of 4 curves and a center thickness of 10 mm, and the other (as Shape 4) had a front surface of 6 curves/back surface of 2 curves and a center thickness of 15.6 mm. The obtained prepared solution was cast in molds with a total of four shapes with five lenses as a number of n for each shape. After casting, polymerization was performed according to the polymerization oven setting temperature program and polymerization ratio shown in FIG. 5, and a lens-shaped resin was obtained through release and annealing. The results of confirming striae of the lens under a high-pressure mercury lamp are shown below for each shape.

Shape 1: n=5 lenses, no striae in 5 lenses
Shape 2: n=5 lenses, no striae in 5 lenses
Shape 3: n=5 lenses, no striae in 5 lenses
Shape 4: n=5 lenses, no striae in 5 lenses As a result, it was possible to obtain an extremely good optical resin in which the generation of striae was suppressed. The Tg of the resin was 113.8° C. The results are shown in Table-3.

Examples 4 to 13

Lenses of Examples 4 to 13 were prepared in the same manner as in Example 3, except that the composition was set as shown in Table-3, and the generation of striae and the Tg were confirmed. The results are shown in Table-3. FIG. 6 to FIG. 15 show the polymerization oven setting temperature programs and polymerization ratios for Examples 4 to 13.

Comparative Example 1

In an apparatus capable of stirring, 239 parts by weight of pentaerythritol tetrakis(3-mercaptopropionate) and 1.00 part by weight of internal release agent for MR were added to 255 parts by weight of 4-mercaptomethyl-1,8-dimercapto-3,6-dithiaoctane, stirring was carried out, 0.2 parts by weight of triethylamine, which was determined to be unusable as a catalyst in Example 1 (Table-1), was added to the solution and stirred. After adjusting the temperature of the solution to 15° C. in a constant temperature bath, 506 parts by weight of a mixture of 2,5-bis(isocyanatomethyl)bicyclo-[2.2.1]-heptane and 2,6-bis(isocyanatomethyl)bicyclo-[2.2.1]-heptane, and 15.0 parts by weight of a UV absorber (VIOSORB 583) were introduced and mixed and stirred at 15° C.

The obtained prepared solution was sufficiently decompressed and degassed, and then returned to atmospheric pressure. At that point, it was not possible to continue with the experiment as the prepared solution rapidly increased in viscosity and increased in temperature due to the polymerization heat. The results are shown in Table-3.

Comparative Example 2

In an apparatus capable of stirring, 239 parts by weight of pentaerythritol tetrakis(3-mercaptopropionate) and 1.00 part by weight of internal release agent for MR were added to 255 parts by weight of 4-mercaptomethyl-1,8-dimercapto-3,6-dithiaoctane, stirring was carried out, 0.02 parts by weight (20 ppm), which was less than the lower limit of the catalyst amount (63 ppm or more and 4231 ppm or less) calculated in Example 2, of 2,4,6-collidine, which is a catalyst, was added to the solution and stirred. After adjusting the temperature of the solution to 15° C. in a constant temperature bath, 506 parts by weight of a mixture of 2,5-bis(isocyanatomethyl)bicyclo-[2.2.1]-heptane and 2,6-bis(isocyanatomethyl)bicyclo-[2.2.1]-heptane, and 15.0 parts by weight of a UV absorber (VIOSORB 583) were introduced and mixed and stirred at 15° C. The obtained prepared solution was sufficiently decompressed and degassed, and then returned to atmospheric pressure.

Figure 16:
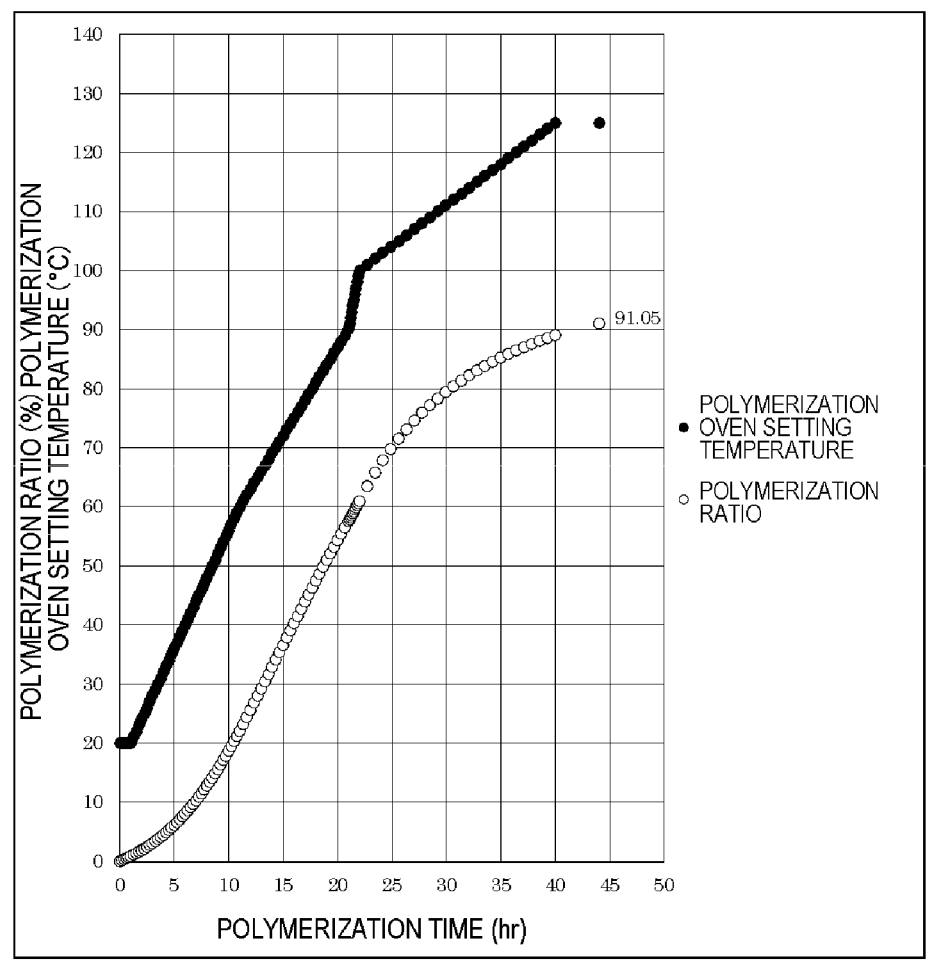
FIG. 16 is a chart plotting a polymerization oven setting temperature for each polymerization time (setting temperature program) and a chart plotting a polymerization ratio for each polymerization time, in Comparative Example 2.

One thin mold (as Shape 1) had a front surface of 2 curves/back surface of 2 curves and a center thickness of 2 mm, and the other (as Shape 2) had a front surface of −400/back surface of FA450 and a center thickness of 1.2 mm. One thick mold (as Shape 3) had a front surface of 6 curves/back surface of 4 curves and a center thickness of 10 mm, and the other (as Shape 4) had a front surface of 6 curves/back surface of 2 curves and a center thickness of 15.6 mm. The obtained prepared solution was cast in molds with a total of four shapes with five lenses as a number of n for each shape. The cast products were polymerized by the polymerization oven setting temperature program shown in FIG. 16 and it was not possible to release all shapes at the time of mold release or to obtain an optical resin. The results are shown in Table-3.

Comparative Example 3

In an apparatus capable of stirring, 255 parts by weight of 4-mercaptomethyl-1,8-dimercapto-3,6-dithiaoctane, 239 parts by weight of pentaerythritol tetrakis(3-mercaptopropionate), and 1.00 part by weight of internal release agent for MR were added, stirring was carried out, and 5 parts by weight (5,000 ppm), which was above the upper limit of the catalyst amount (63 ppm or more and 4,231 ppm or less) calculated in Example 2, of 2,4,6-collidine, which is a catalyst, were added to the solution and stirred. After adjusting the temperature of the solution to 15° C. in a constant temperature bath, 506 parts by weight of a mixture of 2,5-bis(isocyanatomethyl)bicyclo-[2.2.1]-heptane and 2,6-bis(isocyanatomethyl)bicyclo-[2.2.1]-heptane, and 15.0 parts by weight of a UV absorber (VIOSORB 583) were introduced and mixed and stirred at 15° C. The obtained prepared solution was sufficiently decompressed and degassed, and then returned to atmospheric pressure.

Figure 17:
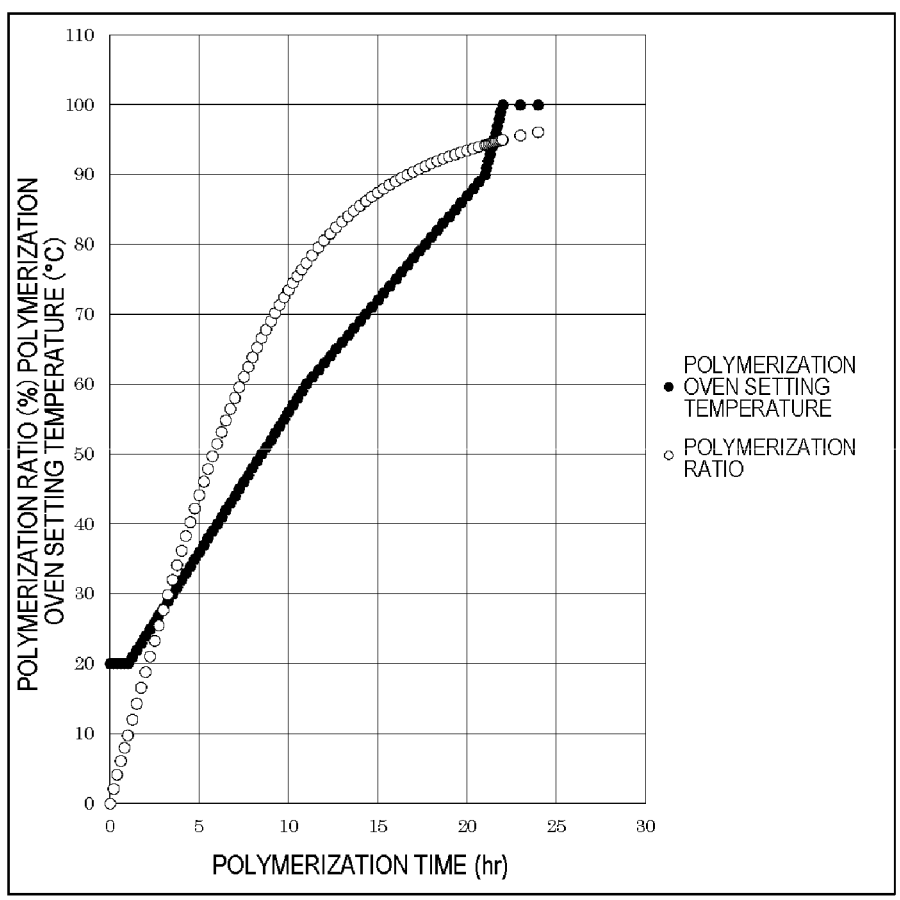
FIG. 17 is a chart plotting a polymerization oven setting temperature for each polymerization time (setting temperature program) and a chart plotting a polymerization ratio for each polymerization time, in Comparative Example 3.

One thin mold (as Shape 1) had a front surface of 2 curves/back surface of 2 curves and a center thickness of 2 mm, and the other (as Shape 2) had a front surface of −400/back surface of FA450 and a center thickness of 1.2 mm. One thick mold (as Shape 3) had a front surface of 6 curves/back surface of 4 curves and a center thickness of 10 mm, and the other (as Shape 4) had a front surface of 6 curves/back surface of 2 curves and a center thickness of 15.6 mm. The obtained prepared solution was cast in molds with a total of four shapes with five lenses as a number of n for each shape. The cast products were polymerized by the polymerization oven setting temperature program shown in FIG. 17, and a lens-shaped resin was obtained through release and annealing. The results of confirming striae of the lens under a high-pressure mercury lamp are shown below for each shape.

Shape 1: n=5 lenses, striae in 5 lenses
Shape 2: n=5 lenses, striae in 5 lenses
Shape 3: n=5 lenses, striae in 5 lenses
Shape 4: n=5 lenses, striae in 5 lenses As a result, it was not possible to obtain an optical resin with no striae. The Tg of the resin was 114.2° C. The results are shown in Table-3.

TABLE 3

| | Thiol compound (parts by weight) | | | Isocyanate compound (parts by weight) | | | | Additive | | Catalyst |
|---|---|---|---|---|---|---|---|---|---|---|
| | a1 | a2 | a3 | b1 | b2 | b3 | b4 | c2 (ppm) | d1 (parts by weight) | Kind |
| Example 3 | 255 | 239 | — | 506 | — | — | — | 1000 | 1.50 | 2,4,6-collidine |
| Example 4 | 255 | 239 | — | 506 | — | — | — | 1000 | 1.50 | N,N-dimethylbenzylamine 3,5-lutidine |
| Example 5 | 255 | 239 | — | 506 | — | — | — | 1000 | 1.50 | 2,4,6-collidine |
| Example 6 | 255 | 239 | — | 506 | — | — | — | 1000 | 1.50 | 2,4,6-collidine |
| Example 7 | 255 | 239 | — | 506 | — | — | — | 1000 | 1.50 | 2,4,6-collidine |
| Example 8 | 255 | 239 | — | 506 | — | — | — | 1000 | 1.50 | 2,4,6-collidine |
| Example 9 | — | — | 507 | — | 493 | — | — | 1000 | 1.50 | 2,4,6-collidine |
| Example 10 | — | 147 | 331 | — | — | 241 | 282 | 1000 | 1.50 | 3,5-lutidine |
| Example 11 | 255 | 239 | — | 506 | — | — | — | 1000 | 1.50 | Dimethyltin dichloride |
| Example 12 | — | — | 507 | — | 493 | — | — | 1000 | 1.50 | Dimethyltin dichloride |
| Example 13 | — | — | 507 | — | 493 | — | — | 1000 | 1.50 | Dimethyltin dichloride |
| Comparative Example 1 | 255 | 239 | — | 506 | — | — | — | 1000 | 1.50 | Triethylamine |
| Comparative Example 2 | 255 | 239 | — | 506 | — | — | — | 1000 | 1.50 | 2,4,6-collidine |
| Comparative Example 3 | 255 | 239 | — | 506 | — | — | — | 1000 | 1.50 | 2,4,6-collidine |

| | Catalyst Added amount (ppm) | Striae evaluation (in five lenses, number of lenses with no striae) | | | | Tg (° C.) |
|---|---|---|---|---|---|---|
| | | Shape 1 | Shape 2 | Shape 3 | Shape 4 | |
| Example 3 | 300 | 5 | 5 | 5 | 5 | 113.8 |
| Example 4 | 50 100 | 5 | 5 | 5 | 5 | 114.5 |
| Example 5 | 300 | 5 | 5 | 5 | 0 | 113.2 |
| Example 6 | 290 | 5 | 5 | 3 | 0 | 114.0 |
| Example 7 | 350 | 5 | 5 | 0 | 0 | 114.1 |
| Example 8 | 300 | 5 | 5 | 0 | 0 | 114.0 |
| Example 9 | 80 | 5 | 5 | 5 | 5 | 102.9 |
| Example 10 | 60 | 5 | 5 | 5 | 5 | 86.2 |
| Example 11 | 350 | 5 | 5 | 5 | 5 | 114.1 |
| Example 12 | 80 | 5 | 5 | 5 | 5 | 103.2 |
| Example 13 | 80 | 5 | 4 | 1 | 1 | 103.2 |
| Comparative Example 1 | 200 | Casting not possible, unable to be implemented | | | | Measuring not possible |
| Comparative Example 2 | 20 | Not released | | | | Measuring not possible |
| Comparative Example 3 | 5000 | 0 | 0 | 0 | 0 | 114.2 |

This application claims priority based on Japanese Application JP 2019-113432 filed on Jun. 19, 2019, the entire disclosure of which is incorporated herein.

REFERENCE SIGNS LIST

1: polymerization catalyst use condition setting apparatus
2: storage unit
10: physical property acquiring unit
20: remaining functional group ratio calculating unit
30: reaction rate constant calculating unit
40: fitting unit
50: polymerization catalyst selecting unit
60: approximation equation setting unit
70: catalyst addition range setting unit
100: polymerization condition setting apparatus
102: storage unit
110: polymerization catalyst amount determining unit
120: reaction rate constant calculating unit
130: polymerization program calculating unit

The invention claimed is:

1. A method for setting conditions for use of a polymerization catalyst, comprising:

providing at least one of a composition 1 or a composition 2, wherein the composition 1 includes a polymerization-reactive compound and a predetermined amount of a polymerization catalyst, wherein the composition 2 is different from the composition 1 only in an amount of the polymerization catalyst;

a physical property acquiring step of, when the composition 1 including a polymerization-reactive compound and a predetermined amount of a polymerization catalyst is heated and maintained at a plurality of temperatures, acquiring a physical property value 1a derived from functional groups of the polymerization-reactive compound before heating and a physical property value 1b derived from remaining functional groups after maintaining a temperature for a predetermined time, and, when the composition 2, which is different from the composition 1 only in an amount of the polymerization catalyst, is heated and maintained at the plurality of temperatures, acquiring a physical property value 2a derived from functional groups of the polymerization-reactive compound before heating and a physical property value 2b derived from remaining functional groups after maintaining a temperature for a predetermined time;

a remaining functional group ratio calculating step of calculating a remaining functional group ratio 1 at the plurality of temperatures from the physical property value 1a and physical property value 1b, and calculating a remaining functional group ratio 2 at the plurality of temperatures from the physical property value 2a and physical property value 2b;

a reaction rate constant calculating step of calculating a reaction rate constant 1 at the plurality of temperatures based on a reaction rate equation from the remaining functional group ratio 1, and calculating a reaction rate constant 2 at the plurality of temperatures based on the reaction rate equation from the remaining functional group ratio 2;

a fitting step of calculating an activation energy $Ea1$ and a frequency factor $A1$ from the reaction rate constant 1 at the plurality of temperatures using an Arrhenius plot, and calculating an activation energy $Ea2$ and a frequency factor $A2$ from the reaction rate constant 2 at the plurality of temperatures using an Arrhenius plot;

a polymerization catalyst selecting step of determining whether the polymerization catalyst satisfies following Condition 1 based on the activation energies $Ea1$ and $Ea2$ or not, Average value of $-Ea1/R$ and $-Ea2/R$ is $-7100$ or more and $-2900$ or less    [Condition 1]

(R: gas constant (8.314 J/mol/K));

an approximation equation setting step of, when the polymerization catalyst is determined to satisfy Condition 1 in the polymerization catalyst selecting step, setting an approximation equation a from two amounts of the polymerization catalyst and the frequency factor $A1$ and the frequency factor $A2$ in the two catalyst amounts, $\ln A = ax + b$    Approximation equation a:

A: Frequency factor
a: Constant determined by the polymerization catalyst
b: Constant determined from two catalyst amounts and frequency factor $A1$ and frequency factor $A2$
x: Added amount of polymerization catalyst to be calculated (ppm); and a catalyst addition range setting step of setting an addition range with respect to the polymerization-reactive compound with a value obtained by multiplying a constant b in the approximation equation a by 1.003 or 1.2 set as the ln A, and each calculated polymerization catalyst added amount x set as a lower limit value and an upper limit value.

2. The method for setting conditions for use of a polymerization catalyst according to claim 1, wherein the catalyst addition range setting step includes a step in which a combination of n kinds (n is an integer of two or more) is selected from the polymerization catalysts, an added amount $x_1$ to an added amount $x_n$ of the n kinds of polymerization catalysts are calculated to satisfy the following condition, and addition ranges of each of the polymerization catalysts are set, $1.003 \leq \{[(a_1 \times x_1 + b_1)/b_1] + [(a_2 \times x_2 + b_2)/b_2] + \ldots + [(a_n \times x_n + b_n)/b_n]\} - (n-1) \leq 1.2$    [Condition]

$a_1$ to $a_n$: Constants determined from n kinds of polymerization catalysts, respectively
$b_1$ to $b_n$: Constants determined from two catalyst amounts and frequency factor $A1$ and frequency factor $A2$, for respective n kinds of polymerization catalysts
$x_1$ to $x_n$: Added amounts of respective n kinds of polymerization catalysts to be calculated (ppm).

3. The method for setting conditions for use of a polymerization catalyst according to claim 1, wherein the physical property values 1a and 1b and the physical property values 2a and 2b are a heat value, a specific gravity, a weight-average molecular weight, a number-average molecular weight, a spectral intensity in IR measurement, a $^1$H-NMR spectral intensity, or a $^{13}$C-NMR spectral intensity.

4. The method for setting conditions for use of a polymerization catalyst according to claim 1, wherein the polymerization catalyst is selected from a tertiary amine compound and an organic tin compound.

5. The method for setting conditions for use of a polymerization catalyst according to claim 1, wherein the polymerization catalyst is selected from 2,4,6-collidine, N,N-dimethylbenzylamine, 3,5-lutidine, dimethyltin dichloride, and dibutyltin dichloride.

6. The method for setting conditions for use of a polymerization catalyst according to claim 1, wherein the polymerization-reactive compound is a polyisocyanate compound and an active hydrogen compound.

7. The method for setting conditions for use of a polymerization catalyst according to claim 6, wherein the polyisocyanate compound is at least one selected from aliphatic polyisocyanate, aromatic polyisocyanate, heterocyclic polyisocyanate, and alicyclic polyisocyanate, and the active hydrogen compound is at least one selected from the group consisting of a polythiol compound having two or more mercapto groups, a hydroxythiol compound having one or more mercapto groups and one or more hydroxyl groups, a polyol compound having two or more hydroxyl groups, and an amine compound.

8. The method for setting conditions for use of a polymerization catalyst according to claim 1, wherein the polymerization-reactive compound is at least one compound selected from an allyl carbonate compound, a (meth)acrylate compound, and an episulfide compound.

9. The method for setting conditions for use of a polymerization catalyst according to claim 8, wherein the allyl carbonate compound is represented by General Formula (1),

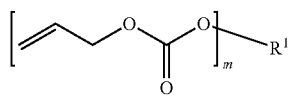

(1)

wherein $R^1$ represents a divalent to 20-valent group derived from a chained or branched aliphatic polyol with 3 to 35 carbon atoms which may include a hetero atom, or a divalent to 20-valent group derived from a cyclic aliphatic polyol with 5 to 40 carbon atoms which may include a hetero atom, m represents an integer of 2 to 10, and $R^1$ does not include an allyloxycarbonyl group.

10. The method for setting conditions for use of a polymerization catalyst according to claim 8, wherein the (meth)acrylate compound is represented by General Formula (2),

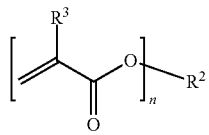

(2)

wherein $R^2$ represents a divalent to tetravalent organic group with 1 to 30 carbon atoms which may include a hetero atom or an aromatic group, $R^3$ represents a hydrogen atom or a methyl group, and n represents an integer of 2 to 4.

11. The method for setting conditions for use of a polymerization catalyst according to claim 8, wherein the episulfide compound is represented by General Formula (3),

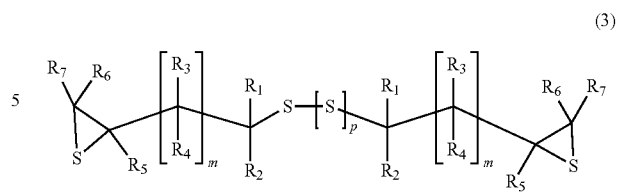

(3)

wherein in General Formula (3), $R_1$ to $R_7$ may be the same or different and represent a hydrogen atom, a linear or branched alkyl group with 1 or more and 10 or fewer carbon atoms, or a substituted or unsubstituted aryl group with 6 or more and 18 or fewer carbon atoms, m represents an integer of 0 or more and 2 or less, and p represents an integer of 0 or more and 4 or less.

12. A polymerization condition setting method comprising:

a polymerization catalyst amount determining step of determining an added amount y of a polymerization catalyst from a kind and an addition range of a polymerization catalyst with respect to a desired polymerizable compound set by the method according to claim 1;

a reaction rate constant calculating step of calculating a reaction rate constant for each of a plurality of reaction temperatures T at the added amount y of the polymerization catalyst in Equation b derived from the approximation equation a and an Arrhenius equation, $$k = \mathrm{Exp}[(-Ea/R) \times (1/T) + (ay+b)]$$ Equation b:

k: Reaction rate constant
−Ea/R: Value included in −7100 or more and −2900 or less, calculated in the polymerization catalyst selecting step
T: Desired reaction temperature (K)
a: Constant determined by the polymerization catalyst
b: Constant determined from two catalyst amounts and frequency factor A1 and frequency factor A2
y: Added amount of polymerization catalyst determined in the polymerization catalyst amount determining step (ppm); and a polymerization program calculating step of back-calculating a polymerization temperature for each predetermined time in a polymerization time based on the reaction rate equation using the reaction rate constant, to satisfy the following conditions, (Conditions)
an average polymerization rate from a 10% polymerization ratio point to an 80% polymerization ratio point is selected and determined in a range of 0.4%/hr or more and 15%/hr or less,
a plurality of polymerization rates are calculated at every predetermined time in a time when a polymerization ratio is 10% or more and 80% or less,
standard deviation, which is a positive square root of a dispersion of the plurality of polymerization rates and the average polymerization rate, is calculated, and
the calculated standard deviation is 2.3%/hr or less.

13. The polymerization condition setting method according to claim 12, wherein the polymerization catalyst amount determining step includes a step of determining n kinds (n is an integer of two or more) of polymerization catalyst kinds and an added amount $y_1$ to an added amount $y_n$ for the respective polymerization catalyst kinds, the reaction rate constant calculating step includes a step in which, in Equation b derived from the approximation equation a and an Arrhenius equation, a reaction rate constant $k_1$ to a reaction rate constant $k_n$ are calculated for each of a plurality of reaction temperatures T at each of added amount $y_1$ to added amount $y_n$ of n kinds of polymerization catalysts, and a reaction rate constant $k_\Sigma$ is calculated for each of the plurality of reaction temperatures T when using n kinds of polymerization catalysts in combination, using equation c, $$k_i = \text{Exp}[(-Ea/R) \times (1/T) + (a_i x_i + b_i)] \quad \text{Equation b:}$$

$k_i$: Reaction rate constants $k_1$ to $k_n$ $-Ea/R$: Value included in $-7100$ or more and $-2900$ or less, calculated in the polymerization catalyst selecting step T: Desired reaction temperature (K)

$a_i$: Constant determined by respective n kinds of polymerization catalysts $b_i$: Constant determined from two catalyst amounts and frequency factor A1 and frequency factor A2 in each of n kinds of polymerization catalysts $x_i$: Added amounts $y_1$ to $y_n$ of each of n kinds of polymerization catalysts (ppm) determined by polymerization catalyst amount determining step $$k_\Sigma = \Sigma_{i=1}^{n} ki \quad \text{Equation c:}$$

n: Integer of 2 or more, and the polymerization program calculating step includes a step of back-calculating a polymerization temperature for each predetermined time in a polymerization time based on a reaction rate equation using the reaction rate constant $k_\Sigma$ so as to satisfy the conditions.

* * * * *